(12) United States Patent
Gambhir et al.

(10) Patent No.: US 7,601,517 B2
(45) Date of Patent: Oct. 13, 2009

(54) SPLIT PROTEIN SELF COMPLEMENTING FRAGMENTS, SYSTEMS, AND METHODS OF USE THEREOF

(75) Inventors: Sanjiv Sam Gambhir, Portola Valley, CA (US); Paulmurugan Ramasamy, Mountain View, CA (US)

(73) Assignee: Stanford University, Palo Alto, CA (US)

( * ) Notice: Subject to any disclaimer, the term of this patent is extended or adjusted under 35 U.S.C. 154(b) by 0 days.

(21) Appl. No.: 11/651,956

(22) Filed: Jan. 10, 2007

(65) Prior Publication Data
US 2007/0161067 A1  Jul. 12, 2007

Related U.S. Application Data

(60) Provisional application No. 60/757,699, filed on Jan. 10, 2006.

(51) Int. Cl.
*C12P 21/04* (2006.01)
*G01N 33/53* (2006.01)
*C12N 9/00* (2006.01)
*C07K 14/00* (2006.01)

(52) U.S. Cl. .............. 435/69.7; 435/7.1; 435/183; 530/350

(58) Field of Classification Search .......... None
See application file for complete search history.

(56) References Cited

U.S. PATENT DOCUMENTS

| | | | |
|---|---|---|---|
| 6,270,964 B1 | 8/2001 | Michnick et al. | 435/6 |
| 6,294,330 B1 | 9/2001 | Michnick et al. | 435/6 |
| 6,428,951 B1 | 8/2002 | Michnick et al. | 435/4 |
| 6,828,099 B2 | 12/2004 | Michnick et al. | 435/6 |
| 6,872,871 B2 | 3/2005 | Brisson et al. | 800/288 |
| 6,897,017 B1 | 5/2005 | Michnick et al. | 435/6 |
| 6,929,916 B2 | 8/2005 | Michnick et al. | 435/6 |
| 7,062,219 B2 | 6/2006 | Michnick et al. | 434/4 |
| 7,160,691 B2 | 1/2007 | Michnick et al. | 435/8 |

OTHER PUBLICATIONS

Ozawa et al. Split Luciferase sa an Optical Probe for Detecting Protein-Protein Interactions in Mammalian Cells Based on Protein Splicing. Analytical Chemistry, 2001, 73(11):2516-2521.*
Luker et al. PNAS, 2004, 101(33):12288-93.*
Ozawa et al., 2006 (available on-line Jul. 11, 2005), Analytica Chimica Acta, vol. 556, pp. 58-68.*
Buskirk et al. PNAS, 2004, 101(29):10505-10510.*
Lougheed et al. Crystal Structures of the Phosphorylated and Unphosphorylated Kinase Domains of the Cdc42-associated Tyrosine Kinase ACK1. JBC Papers in Press, published Aug. 11, 2004, pp. 1-40. (www.jbc.org/cgi/reprint/M406703200v1.pdf).*

* cited by examiner

*Primary Examiner*—Suzanne M. Noakes
(74) *Attorney, Agent, or Firm*—Thomas, Kayden, Horstemeyer & Risley LLP

(57) ABSTRACT

Briefly described, embodiments of this disclosure include split protein systems, fusion proteins, methods of producing the split protein systems, methods of screening macromolecular delivery vehicles, methods of cellular localization of proteins, methods of monitoring cell fusion, methods of detecting phosphorylation, and the like.

33 Claims, 8 Drawing Sheets

SEQUENCE LISTING

<160> NUMBER OF SEQ ID NOS: 2

<210> SEQ ID NO 1
<211> LENGTH: 1653
<212> TYPE: DNA
<213> ORGANISM: Firefly Luciferase

<400> SEQUENCE: 1

```
atggaagacg ccaaaaacat aaagaaaggc ccggcgccat tctatccgct ggaagatgga      60
accgctggag agcaactgca taaggctatg aagagatacg ccctggttcc tggaacaatt     120
gcttttacag atgcacatat cgaggtggac atcacttacg ctgagtactt cgaaatgtcc     180
gttcggttgg cagaagctat gaaacgatat gggctgaata caaatcacag aatcgtcgta     240
tgcagtgaaa actctcttca attctttatg ccggtgttgg gcgcgttatt tatcggagtt     300
gcagttgcgc ccgcgaacga catttataat gaacgtgaat tgctcaacag tatgggcatt     360
tcgcagccta ccgtggtgtt cgtttccaaa aagggggttgc aaaaaatttt gaacgtgcaa     420
aaaaagctcc caatcatcca aaaaattatt atcatggatt ctaaaacgga ttaccaggga     480
tttcagtcga tgtacacgtt cgtcacatct catctacctc ccggttttaa tgaatacgat     540
tttgtgccag agtccttcga tagggacaag acaattgcac tgatcatgaa ctcctctgga     600
tctactggtc tgcctaaagg tgtcgctctg cctcatagaa ctgcctgcgt gagattctcg     660
catgccagag atcctatttt tggcaatcaa atcattccgg atactgcgat tttaagtgtt     720
gttccattcc atcacggttt tggaatgttt actacactcg gatatttgat atgtggattt     780
cgagtcgtct taatgtatag atttgaagaa gagctgtttc tgaggagcct tcaggattac     840
aagattcaaa gtgcgctgct ggtgccaacc ctattctcct tcttcgccaa agcactctg      900 attgacaaat acgatttatc taatttacac gaaattgctt ctggtggcgc tcccctctct     960
aaggaagtcg gggaagcggt tgccaagagg ttccatctgc caggtatcag gcaaggatat    1020
gggctcactg agactacatc agctattctg attacacccg agggggatga taaaccgggc    1080
gcggtcggta aagttgttcc attttttgaa gcgaaggttg tggatctgga taccgggaaa    1140
```

-continued

```
acgctgggcg ttaatcaaag aggcgaactg tgtgtgagag gtcctatgat tatgtccggt    1200
tatgtaaaca atccggaagc gaccaacgcc ttgattgaca aggatggatg gctacattct    1260
ggagacatag cttactggga cgaagacgaa cacttcttca tcgttgaccg cctgaagtct    1320
ctgattaagt acaaaggcta tcaggtggct cccgctgaat tggaatccat cttgctccaa    1380 cacccccaaca tcttcgacgc aggtgtcgca ggtcttcccg acgatgacgc cggtgaactt    1440
cccgccgccg ttgttgtttt ggagcacgga agacgatga cggaaaaaga gatcgtggat    1500
tacgtcgcca gtcaagtaac aaccgcgaaa aagttgcgcg gaggagttgt gtttgtggac    1560
gaagtaccga aaggtcttac cggaaaactc gacgcaagaa aaatcagaga gatcctcata    1620
aaggccaaga agggcggaaa gatcgccgtg taa                                 1653
```

<210> SEQ ID NO 2
<211> LENGTH: 549
<212> TYPE: PRT
<213> ORGANISM: Firefly Luciferase

<400> SEQUENCE: 2

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
```

```
                    275                 280                 285
Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
                340                 345                 350

Pro Glu Gly Asp Asp Lys Pro Gly Gly Val Gly Lys Val Val Pro Phe
                355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Asp Ile Ala Tyr Trp Asp Glu Asp Glu His Phe Phe
                420                 425                 430

Ile Val Asp Arg Leu Lys Ser Leu Ile Lys Tyr Lys Gly Tyr Gln Val
                435                 440                 445

Ala Pro Ala Glu Leu Glu Ser Ile Leu Leu Gln His Pro Asn Ile Phe
    450                 455                 460

Asp Ala Gly Val Ala Gly Leu Pro Asp Asp Asp Ala Gly Glu Leu Pro
465                 470                 475                 480

Ala Ala Val Val Val Leu Glu His Gly Lys Thr Met Thr Glu Lys Glu
                485                 490                 495

Ile Val Asp Tyr Val Ala Ser Gln Val Thr Thr Ala Lys Lys Leu Arg
                500                 505                 510

Gly Gly Val Val Phe Val Asp Glu Val Pro Lys Gly Leu Thr Gly Lys
            515                 520                 525

Leu Asp Ala Arg Lys Ile Arg Glu Ile Leu Ile Lys Ala Lys Lys Gly
            530                 535                 540

Gly Lys Ser Lys Leu
545
```

SPLIT PROTEIN SELF COMPLEMENTING FRAGMENTS, SYSTEMS, AND METHODS OF USE THEREOF

CROSS-REFERENCE TO RELATED APPLICATION

This application claims priority to U.S. provisional application entitled, "Split Protein Self Complementing Fragments, Systems, and Methods of Use Thereof," having Ser. No. 60/757,699, filed on Jan. 10, 2006, which is entirely incorporated herein by reference.

STATEMENT REGARDING FEDERALLY SPONSORED RESEARCH OR DEVELOPMENT

This invention was made with Government support under contracts CA082214 and CA114747 awarded by the National Institutes of Health. The Government has certain rights in this invention.

BACKGROUND

Luciferases are enzymes that emit light in reaction with a specific substrate in the presence of co-factors. A diverse group of organisms use luciferase-mediated bioluminescence to startle predators or to attract prey or mates. The emitted light is used as a detection system for luciferase expression, which acts as a "reporter" for the activity of any regulatory element that controls its expression. Luciferase is particularly useful as a reporter enzyme in living cells and organisms. Firefly luciferase is one of many sensitive luciferases and is widely used by researchers to identify different biological events of cells in culture and in living small animals, and it is also used by public health researchers for the detection of food contamination.

The gene encoding firefly luciferase, cloned in 1985 from the North American firefly, *Photinus pyralis* is now emerging as the gene of choice for in vivo and in vitro reporting of transcriptional activity in eukaryotic cells. Reporter genes encoding for proteins with optical signatures, either fluorescent or bioluminescent, are a low-cost alternative for real-time analysis of gene expression in small animal models. In fluorescent approaches an external source of light is required for excitation of the protein. In contrast, bioluminescent reporter proteins can only produce light by using the appropriate substrates. Recently, several technical advances in utilizing highly sensitive detection devices have led to the biological use of cooled charge-coupled device (CCD) cameras capable of imaging very low levels of visible light emitted from internal organs of rodents. "Luciferase" is a family of photo-proteins that can be isolated from a large variety of insects, marine organisms, and prokaryotes. The emission spectrum ranges between 400 nm and 620 nm.

Functional proteins are made up of one or more polypeptides. Monomeric functional proteins can be split into two portions with resulting functionally inactive fragments. These split reporters have been used for measuring real time protein-protein interactions efficiently, both in cells and also in living animals. The inactive protein fragment assisted complementation of dihydrofolate reductase and β-lactamase have been used for studying protein-protein interactions in bacteria and mammalian cells. In previous studies, split bioluminescent monomeric proteins such as firefly luciferase and synthetic *renilla* luciferase, and the resulting fragments were used for studying protein-protein interactions. This was demonstrated by studying two known positive interacting proteins Id and myoD, and also by small molecule Rapamycin mediated interaction of human proteins FRB and FKBP12 in both cell culture and with noninvasive repetitive bioluminescence optical imaging in living mice. For many proteins, the backbones of the polypeptide chain have been split by chemical, proteolytic or genetic means and have created inter-chain packed active functional proteins. This combination of two protein fragments to restore activity has been termed as protein fragment complementation. The generation of functional proteins from a monomeric form to a heterodimeric form has been hypothesized as the phenomenon of the reversion of evolutionary process in which functional structures or domains are recruited and then fused at the genetic level. Even though many studies have reported the use of fragment-assisted complementation of optical reporter proteins for studying protein-protein interactions, we are not aware of any reports on the self-complementation of any of these reporters.

SUMMARY

Briefly described, embodiments of this disclosure include split protein systems, fusion proteins, methods of producing the split protein systems, methods of screening macromolecular delivery vehicles, methods of cellular localization of proteins, method of monitoring cell fusion, methods of detecting phosphorylation, and the like.

An embodiment of a split protein system, among others, includes: a first protein including a first self complementing fragment, wherein the first self complementing fragment comprises a first portion of a firefly Luciferase protein, and a second protein including a second self complementing fragment, wherein the second self complementing fragment comprises a second portion of a firefly Luciferase protein complementary with the first self complementing fragment, wherein the first self complementing fragment and the second self complementing fragment are not bioluminescent individually, and wherein the first self complementing fragment and the second self complementing fragment spontaneously self complement to substantially form the firefly Luciferase protein that is bioluminescent.

An embodiment of a method of producing the split protein system, among others, includes: providing a first vector that includes a first polynucleotide that encodes a first protein including a first self complementing fragment, wherein the first self complementing fragment comprises a first portion of a firefly Luciferase protein; expressing the first polynucleotide to produce the first fusion protein in a first system; providing a second vector that includes a second polynucleotide sequence that encodes a second protein including a second self complementing fragment, wherein the second self complementing fragment comprises a second portion of a firefly Luciferase protein complementary with the first self complementing fragment, wherein the first self complementing fragment and the second self complementing fragment are not bioluminescent individually, and wherein the first self complementing fragment and the second self complementing fragment spontaneously self complement to substantially form the firefly Luciferase protein that is bioluminescent; and expressing the second polynucleotide to produce the second protein in a second system.

An embodiment of a method of screening macromolecular delivery vehicles, among others, includes: providing a first protein including a first target and a first self complementing fragment, wherein the first self complementing fragment comprises a first portion of a firefly Luciferase protein, wherein first target is a macromolecular delivery vehicle; exposing the first protein to a cell, wherein the cell comprises a second protein including a second self complementing fragment, wherein the second self complementing fragment comprises a second portion of the firefly Luciferase protein complementary with the first self complementing fragment, wherein the first self complementing fragment and the second self complementing fragment are not bioluminescent individually, and wherein the first self complementing fragment and the second self complementing fragment spontaneously self complement to substantially form the firefly Luciferase protein; and generating a bioluminescent signal if the first protein enters the cell and the first self complementing fragment spontaneously self complements with the second self complementing fragment in the presence of a bioluminescence initiating compound, wherein if the bioluminescent signal is generated the macromolecular delivery vehicle entered the cell.

Another embodiment of a method of screening macromolecular delivery vehicles, among others, includes: providing a first protein including a first target and a first self complementing fragment, wherein the first self complementing fragment comprises a first portion of a firefly Luciferase protein wherein first target is a macromolecular delivery vehicle; providing a second vector that includes a polynucleotide sequence that encodes a second protein including a second self complementing fragment, wherein the second self complementing fragment comprises a second portion of the firefly Luciferase protein complementary with the first self complementing fragment, wherein the first self complementing fragment and the second self complementing fragment are not bioluminescent individually, and wherein the first self complementing fragment and the second self complementing fragment spontaneously self complement to substantially form the firefly Luciferase protein; expressing the second polynucleotide to produce the second protein in the cell; and generating a bioluminescent signal if the first protein enters the cell and the first self complementing fragment spontaneously self complements with the second self complementing fragment in the presence of a bioluminescence initiating compound, wherein if the bioluminescent signal is generated the macromolecular delivery vehicle entered the cell.

An embodiment of a method of cellular localization of proteins, among others, includes: providing a first protein including a first target protein and a first self complementing fragment, wherein the first self complementing fragment comprises a first portion of a firefly Luciferase protein; exposing the first protein to a cell, wherein a compartment of the cell comprises a second protein including a second self complementing fragment, wherein the second self complementing fragment comprises a second portion of the firefly Luciferase protein complementary with the first self complementing fragment, wherein the first self complementing fragment and the second self complementing fragment are not bioluminescent individually, and wherein the first self complementing fragment and the second self complementing fragment spontaneously self complement to substantially form the firefly Luciferase protein; and generating a bioluminescent signal if the first protein enters the compartment and the first self complementing fragment spontaneously self complements with the second self complementing fragment in the presence of a bioluminescence initiating compound, wherein if the bioluminescent signal is generated the first target protein entered the cell compartment.

Another embodiment of a method of cellular localization of proteins, among others, includes: providing a first protein including a first target protein and a first self complementing fragment, wherein the first self complementing fragment comprises a first portion of a firefly Luciferase protein; providing a second vector that includes a second polynucleotide sequence that encodes a second protein including a second self complementing fragment, wherein the second self complementing fragment comprises a second portion of the firefly Luciferase protein complementary with the first self complementing fragment, wherein the first self complementing fragment and the second self complementing fragment are not bioluminescent individually, and wherein the first self complementing fragment and the second self complementing fragment spontaneously self complement to substantially form the firefly Luciferase protein; expressing the second polynucleotide to produce the second protein in a compartment of a cell; and generating a bioluminescent signal if the first protein enters the compartment and the first self complementing fragment spontaneously self complements with the second self complementing fragment in the presence of a bioluminescence initiating compound, wherein if the bioluminescent signal is generated the first target protein entered the cell compartment.

An embodiment of a method of monitoring cell fusion, among others, includes: providing a first cell that comprises a first self complementing fragment, wherein the first self complementing fragment comprises a first portion of a firefly Luciferase protein; providing a second cell that comprises a second self complementing fragment, wherein the second self complementing fragment comprises a second portion of a firefly Luciferase protein complementary with the first self complementing fragment, wherein the first self complementing fragment and the second self complementing fragment are not bioluminescent individually, and wherein the first self complementing fragment and the second self complementing fragment spontaneously self complement to substantially form the firefly Luciferase protein; and co-culturing the first cell with the second cell, wherein if cell-cell fusion between the first cell and the second cell occurs, a bioluminescent signal is generated when the first self complementing fragment spontaneously self complements with the second self complementing fragment in the presence of a bioluminescence initiating compound.

Another embodiment of a method of monitoring cell fusion, among others, includes: providing a first vector that includes a first polynucleotide that encodes a first protein that includes a first self complementing fragment, wherein the first complementing fragment comprises a first portion of a firefly Luciferase protein; expressing the first polynucleotide to produce the first protein in a first cell; providing a second vector that includes a second polynucleotide sequence that encodes a second protein that includes a second self complementing fragment, wherein the second self complementing fragment comprises a second portion of a firefly Luciferase protein complementary with the first self complementing fragment, wherein the first self complementing fragment and the second self complementing fragment are not bioluminescent individually, and wherein the first self complementing fragment and the second self complementing fragment spontaneously self complement to substantially form the firefly Luciferase protein; expressing the second polynucleotide to produce the second protein in a second cell; and co-culturing the first cell with the second cell, wherein if cell-cell fusion between the first cell and the second cell occurs, a bioluminescent signal is generated when the first self complementing fragment spontaneously self complements with the second self complementing fragment in the presence of a bioluminescence initiating compound.

An embodiment of a method of detecting phosphorylation, among others, includes: providing a fusion protein including a first self complementing fragment and a second self complementing fragment, wherein a phosphotyrosine binding substrate is attached to a first end of the first self complementing fragment, wherein a phosphotyrosine peptide is attached to the first end of the second self complementing fragment, wherein a linker peptide is attached to each of the phosphotyrosine binding substrate and the phosphotyrosine peptide to form a continuous structure in the following order: the first self complementing fragment, the phosphotyrosine binding substrate, the linker peptide, the phosphotyrosine peptide, and the second self complementing fragment; wherein the linker peptide is rigid to separate the first self complementing fragment and the second self complementing fragment until phosphorylation is initiated between the phosphotyrosine binding substrate the phosphotyrosine peptide, wherein the first self complementing fragment and the second self complementing fragment are not bioluminescent, and wherein the first self complementing fragment and the second self complementing fragment spontaneously self complement to substantially form the firefly Luciferase protein; initiating phosphorylation between the phosphotyrosine binding substrate the phosphotyrosine peptide; and generating a bioluminescent signal when the first self complementing fragment spontaneously self complements with the second self complementing fragment in the presence of a bioluminescence initiating compound if phosphorylation occurs between the phosphotyrosine binding substrate and the phosphotyrosine peptide.

An embodiment of a method of detecting phosphorylation, among others, includes: a first self complementing fragment and a second self complementing fragment; a phosphotyrosine binding substrate attached to a first end of the first self complementing fragment; a phosphotyrosine peptide attached to the first end of the second self complementing fragment; and a linker peptide attached to each of the phosphotyrosine binding substrate and the phosphotyrosine peptide, wherein the fusion peptide forms a continuous structure in the following order: the first self complementing fragment, the phosphotyrosine binding substrate, the linker peptide, the phosphotyrosine peptide, and the second self complementing fragment, wherein the linker peptide is rigid to separate the first self complementing fragment and the second self complementing fragment until phosphorylation is initiated between the phosphotyrosine binding substrate the phosphotyrosine peptide, wherein the first self complementing fragment and the second self complementing fragment are not bioluminescent, and wherein the first self complementing fragment and the second self complementing fragment spontaneously self complement to substantially form the firefly Luciferase protein if phosphorylation occurs between the phosphotyrosine binding substrate and the phosphotyrosine peptide.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
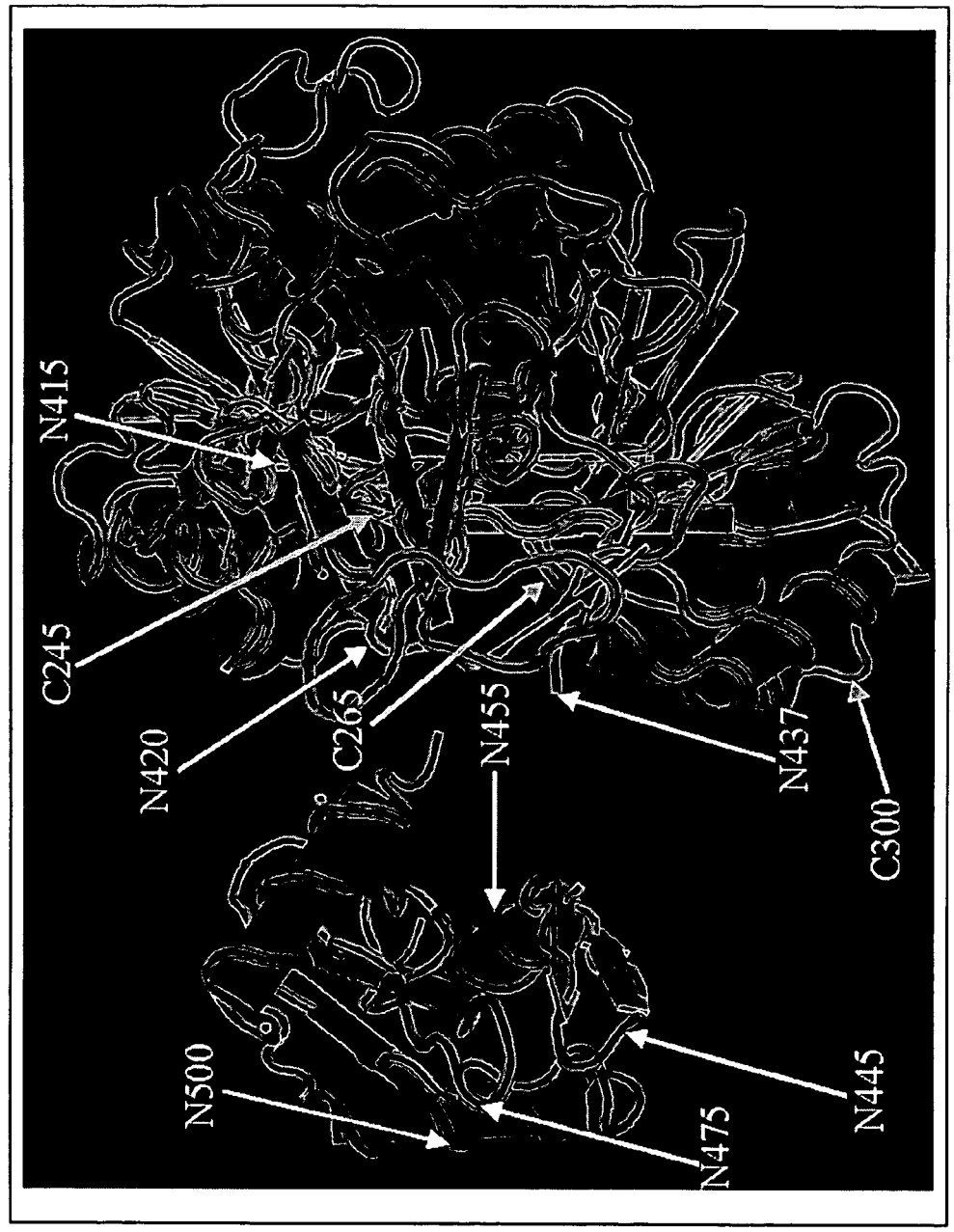
FIG. 1 illustrates a schematic diagram showing the three dimensional structure of firefly luciferase enzyme with indicated sites used for generating different $NH_2$ and COOH terminal fragments for the fragment self-complementation strategy.
Figure 2:
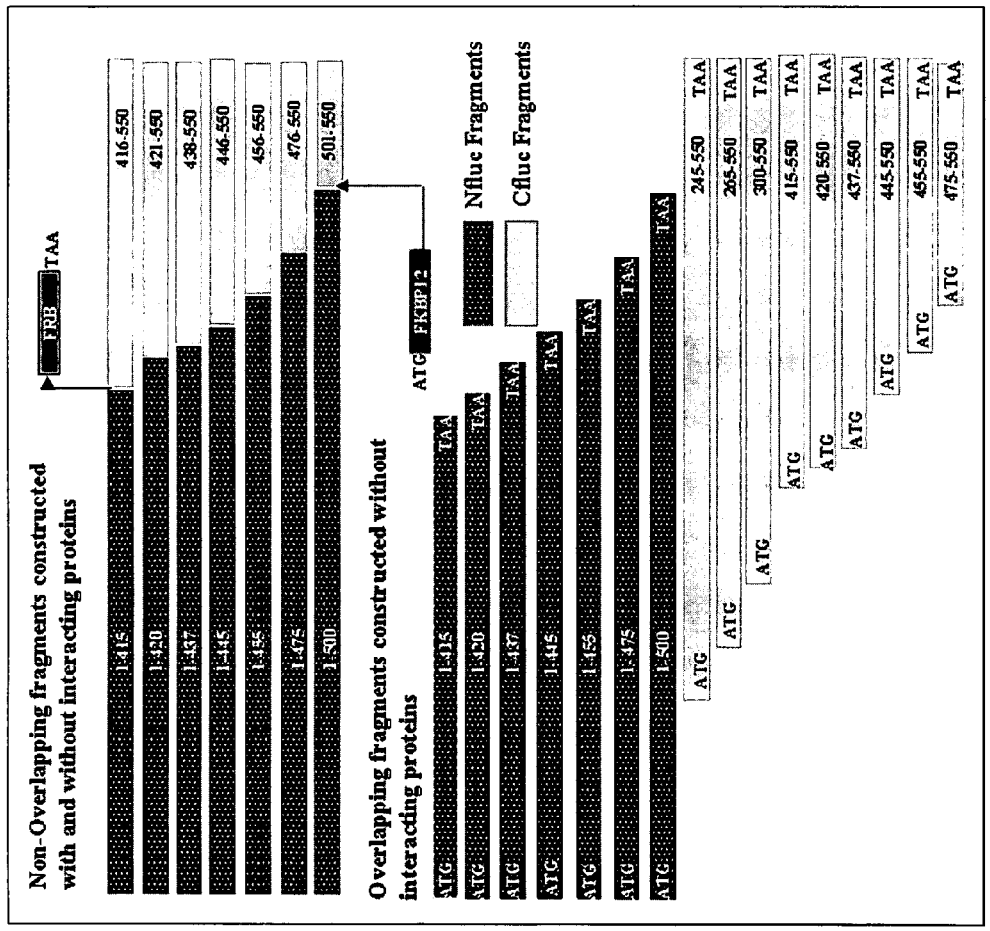
FIG. 2 illustrates a schematic diagram showing different vector constructs generated for the self-complementation study for overlapping and non-overlapping luciferase enzyme fragments with and without interacting proteins (FRB/FKBP12). The split sites are indicated after the amino acid positions.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Embodiments of the present disclosure will employ, unless otherwise indicated, techniques of synthetic organic chemistry, biochemistry, molecular biology, and the like, that are within the skill of the art. Such techniques are explained fully in the literature.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of synthetic organic chemistry, biochemistry, biology, molecular biology, pharmacology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible. It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

Definitions

In describing and claiming the disclosed subject matter, the following terminology will be used in accordance with the definitions set forth below.

The term "complementing fragments" or "complementary fragments" when used in reference to a reporter polypeptide refer to fragments of a polypeptide that are individually inactive (e.g., do not express the reporter phenotype), wherein binding of the complementing fragments restores reporter activity. The terms "self-complementing", "self-assembling", and "spontaneously-associating", when used to describe two fragments of the same protein, mean that the fragments are capable of reconstituting into an active, bioluminescent protein when the individual fragments are soluble and are sufficiently close to or contact one another.

"Bioluminescent initiator molecule" is a molecule that can react with a bioluminescent protein to generate bioluminescence.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

In addition, the protein can include non-standard and/or non-naturally occurring amino acids, as well as other amino acids that may be found in phosphorylated proteins in organisms such as, but not limited to, animals, plants, insects, protists, fungi, bacteria, algae, single-cell organisms, and the like. The non-standard amino acids include, but are not limited to, selenocysteine, pyrrolysine, gamma-aminobutyric acid, carnitine, ornithine, citrulline, homocysteine, hydroxyproline, hydroxylysine, sarcosine, and the like. The non-naturally occurring amino acids include, but are not limited to, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homo-glutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine.

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also refers to the degree of sequence relatedness between polypeptide as determined by the match between strings of such sequences. "Identity" and "similarity" can be readily calculated by known methods, including, but not limited to, those described in Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073, (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970)

algorithm (e.g., NBLAST, and XBLAST). The default parameters are used to determine the identity for the polypeptides of the present invention.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence, or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

Conservative amino acid variants can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxyethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenyl-alanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. (Robertson, et al., *J. Am. Chem. Soc.*, 113: 2722, 1991; Ellman, et al., *Methods Enzymol.*, 202: 301, 1991; Chung, et al., *Science*, 259: 806-9, 1993; and Chung, et al., *Proc. Natl. Acad. Sci. USA*, 90: 10145-9, 1993). In a second method, translation is carried out in *Xenopus* oocytes by microinjection of mutated mRNA and chemically aminoacylated suppressor tRNAs (Turcatti, et al., *J. Biol. Chem.*, 271: 19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. (Koide, et al., *Biochem.*, 33: 7470-6, 1994). Naturally occurring amino acid residues can be converted to non-naturally occurring species by in vitro chemical modification. Chemical modification can be combined with site-directed mutagenesis to further expand the range of substitutions (Wynn, et al., *Protein Sci.*, 2: 395-403, 1993).

As used herein, the term "polynucleotide" generally refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid," "nucleic acid sequence," or "oligonucleotide" also encompass a polynucleotide as defined above.

In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically, or metabolically modified forms of polynucleotides, as well as the chemical forms of DNA and RNA characteristic of viruses and cells, including simple and complex cells, inter alia.

By way of example, a polynucleotide sequence of the present disclosure may be identical to the reference sequence, that is be 100% identical, or it may include up to a certain integer number of nucleotide alterations as compared to the reference sequence. Such alterations are selected from the group including at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the reference nucleotide by the numerical percent of the respective percent identity (divided by 100) and subtracting that product from said total number of nucleotides in the reference nucleotide. Alterations of a polynucleotide sequence encoding the polypeptide may alter the polypeptide encoded by the polynucleotide following such alterations.

The term "codon" means a specific triplet of mononucleotides in the DNA chain. Codons correspond to specific amino acids (as defined by the transfer RNAs) or to start and stop of translation by the ribosome.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (e.g., GAU and GAC triplets each encode Asp).

A DNA "coding sequence" is a DNA sequence that is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence may be located 3' to the coding sequence.

"Operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will direct the linked protein to be localized at the specific organelle.

As used herein, the term "exogenous DNA" or "exogenous nucleic acid sequence" or "exogenous polynucleotide" refers to a nucleic acid sequence that was introduced into a cell or organelle from an external source. Typically the introduced exogenous sequence is a recombinant sequence.

A cell has been "transformed" or "transfected" by a nucleic acid sequence such as an exogenous or a heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transfected cell is one in which the transected DNA has become integrated into a chromosome so that it is inherited by daughter cells through chromosome replication. This stability is demonstrated by the ability of the eukaryotic cell to establish cell lines or clones comprised of a population of daughter cells containing the transfected DNA. A "clone" is a population of cells derived from a single cell or common ancestor by mitosis. A "cell line" is a clone of a primary cell that is capable of stable growth in vitro for many generations. The nucleic acid may be in the form of naked DNA or RNA, associated with various proteins or the nucleic acid may be incorporated into a vector.

A "heterologous" region of a DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, heterologous DNA includes coding sequence in a construct where portions of genes from two different sources have been brought together so as to produce a fusion protein product. Allelic variations or naturally-occurring mutational events do not give rise to a heterologous region of DNA as defined herein.

As used herein, the term "vector" or "expression vector" is used to denote a DNA molecule, linear or circular, which includes a segment encoding a polypeptide of interest operably linked to additional segments that provide for its transcription and translation upon introduction into a host cell or host cell organelles. Such additional segments include promoter and terminator sequences, and may also include one or more origins of replication, one or more selectable markers, an enhancer, a polyadenylation signal, etc. Expression vectors are generally derived from yeast or bacterial genomic or plasmid DNA, or viral DNA, or may contain elements of one or more of the above.

"DNA regulatory sequences", as used herein, are transcriptional and translational control sequences, such as promoters, enhancers, polyadenylation signals, terminators, and the like, that provide for and/or regulate expression of a coding sequence in a host cell.

A "promoter sequence" is a DNA regulatory region capable of binding RNA polymerase in a cell and initiating transcription of a downstream (towards 3' direction) coding sequence. For purposes of defining the present disclosure, the promoter sequence is bounded at its 5' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present disclosure.

As used herein, the terms "restriction endonucleases" and "restriction enzymes" refer to bacterial enzymes, each of which cut double-stranded DNA at or near a specific nucleotide sequence.

As used herein, the term "hybridization" refers to the process of association of two nucleic acid strands to form an antiparallel duplex stabilized by means of hydrogen bonding between residues of the opposite nucleic acid strands.

The term "immunologically active" defines the capability of the natural, recombinant or synthetic bioluminescent protein, or any oligopeptide thereof, to induce a specific immune response in appropriate animals or cells and to bind with specific antibodies. As used herein, "antigenic amino acid sequence" means an amino acid sequence that, either alone or in association with a carrier molecule, can elicit an antibody response in a mammal. The term "specific binding," in the context of antibody binding to an antigen, is a term well understood in the art and refers to binding of an antibody to the antigen to which the antibody was raised, but not other, unrelated antigens.

As used herein the term "isolated" is meant to describe a polynucleotide, a polypeptide, an antibody, or a host cell that is in an environment different from that in which the polynucleotide, the polypeptide, the antibody, or the host cell naturally occurs.

"Optional" or "optionally" means that the subsequently described circumstance may or may not occur, so that the description includes instances where the circumstance occurs and instances where it does not.

"Hybridizing" and "binding", with respect to polynucleotides, are used interchangeably. The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions.

The term "salts" herein refers to both salts of carboxyl groups and to acid addition salts of amino groups of the polypeptides of the present disclosure. Salts of a carboxyl group may be formed by methods known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Any of such salts should have substantially similar activity to the peptides and polypeptides of the present disclosure or their analogs.

The polynucleotides and the vectors can be introduced into cells with different purposes, generating transgenic cells and organisms. A process for producing cells capable of expressing a polypeptide of the present disclosure includes genetically engineering cells with such vectors and nucleic acids.

In particular, host cells (e.g., bacterial cells) can be modified by transformation for allowing the transient or stable expression of the polypeptides encoded by the nucleic acids and the vectors of the present disclosure. Alternatively, the molecules can be used to generate transgenic animal cells or non-human animals (by non-/homologous recombination or by any other method allowing their stable integration and maintenance), having enhanced or reduced expression levels of the polypeptides of the present disclosure, when the level is compared with the normal expression levels. Such precise modifications can be obtained by making use of the nucleic acids of the present disclosure and of technologies associated, for example, to gene therapy (Meth. Enzymol., vol. 346, 2002) or to site-specific recombinases (Kolb A F, 2002).

Gene silencing approaches may also be undertaken to down-regulate endogenous expression of a gene encoding a polypeptide of the present disclosure. RNA interference (RNAi) (Elbashir, S M et al., Nature 2001, 411, 494-498) is one method of sequence specific post-transcriptional gene silencing that may be employed. Short dsRNA oligonucleotides are synthesised in vivo and introduced into a cell. The sequence specific binding of these dsRNA oligonucleotides triggers the degradation of target mRNA, reducing or ablating target protein expression.

Efficacy of the gene silencing approaches assessed above may be assessed through the measurement of polypeptide expression (for example, by Western blotting), and at the RNA level using TaqMan-based methodologies.

The polypeptides of the present disclosure can be prepared by any method known in the art, including recombinant DNA-related technologies, and chemical synthesis technologies. In particular, a method for making a polypeptide of the present disclosure may include culturing a host or transgenic cell as described above under conditions in which the nucleic acid or vector is expressed, and recovering the polypeptide encoded by said nucleic acid or vector from the culture. For example, when the vector expresses the polypeptide as a fusion protein with an extracellular or signal-peptide containing proteins, the recombinant product can be secreted in the extracellular space, and can be more easily collected and purified from cultured cells in view of further processing or, alternatively, the cells can be directly used or administered.

The DNA sequence coding for the proteins of the present disclosure can be inserted and ligated into a suitable episomal or non-/homologously integrating vectors, which can be introduced in the appropriate host cells by any suitable means (transformation, transfection, conjugation, protoplast fusion, electroporation, calcium phosphate-precipitation, direct microinjection, etc.). Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

The vectors should allow the expression of the isolated or fusion protein including the polypeptide of the disclosure in the prokaryotic or eukaryotic host cells under the control of transcriptional initiation/termination regulatory sequences, which are chosen to be constitutively active or inducible in the host cell. A cell line substantially enriched in such cells can be then isolated to provide a stable cell line.

For eukaryotic hosts (e.g., yeasts, insect cells, plant cells, or mammalian cells), different transcriptional and translational regulatory sequences may be employed, depending on the nature of the host. They may be derived form viral sources, such as adenovirus, bovine papilloma virus, Simian virus or the like, where the regulatory signals are associated with a particular gene, which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated. The cells stably transfected by the introduced DNA can be selected by introducing one or more markers allowing the selection of host cells which contain the expression vector. The marker may also provide for prototrophy to an auxotropic host biocide resistance, e.g., antibiotics, or heavy metals such as copper, or the like. The selectable marker gene can either be directly linked to the DNA gene sequences to be expressed, or introduced into the same cell by co-transfection.

Host cells may be either prokaryotic or eukaryotic. Preferred are eukaryotic hosts, e.g., mammalian cells, such as human, monkey, mouse, and Chinese Hamster Ovary (CHO) cells, because they provide post-translational modifications to proteins, including correct folding and glycosylation. Also yeast cells can carry out post-translational peptide modifications including glycosylation. A number of recombinant DNA strategies exist that utilize strong promoter sequences and high copy number of plasmids, which can be utilized for production of the desired proteins in yeast. Yeast recognizes leader sequences in cloned mammalian gene products and secretes peptides bearing leader sequences (i.e., pre-peptides).

As used herein, the term "organelle" refers to cellular membrane bound structures such as the chloroplast, mitochondrion, and nucleus. The term "organelle" includes natural and synthetic organelles.

As used herein, the term "non-nuclear organelle" refers to any cellular membrane bound structure present in a cell, except the nucleus.

As used herein, the term "host" or "organism" includes humans, mammals (e.g., mice, rates, cats, dogs, horses, etc.), living cells, and other living organisms. A living organism can be as simple as, for example, a single eukaryotic cell or as complex as a mammal.

General Discussion

In general, the present disclosure includes split protein self complementing fragments, split protein self complementing systems, methods of cellular localization of proteins, methods of screening macromolecular delivery systems, methods of monitoring cell-cell fusion, methods of using split protein self complementing fragments for detecting phosphorylation, methods of detecting phosphorylation, and the like. In addition, embodiments of this disclosure, among others, include fusion proteins including split protein self complementing fragments, vectors encoding split protein self complementing fragments, and methods of using the fusion proteins, the vectors, and the like.

In general, a split protein self complementing system includes a first self complementing fragment and a second self complementing fragment that are initially separated. Then, if the first self complementing fragment and the second self complementing fragment come into contact with one another, they spontaneously self complement (e.g., inherent self affinity between the protein fragments brings the fragments close to each other and generates an event called complementation, as described in more detail below) to form a bioluminescent protein. The bioluminescent protein can produce a bioluminescent emission upon interaction with a bioluminescence initiating compound.

Although embodiments of the split protein self complementing fragments are not bioluminescent when separated, the split protein self complementing fragments are able to spontaneously self complement upon coming into sufficiently close contact with one another to form a bioluminescent protein (e.g., a firefly Luciferase protein or variant thereof), which can be bioluminescent upon interaction with a bioluminescence initiating compound. In this regard, the split protein self complementing fragments can be used to detect, study, monitor, evaluate, and/or screen, biological or cellular events, such as, but not limited to, protein-protein interactions, cellular localization of proteins, protein phosphorylation, cell-cell fusion, interactions of macromolecule delivery vehicle with cells, and the like. In an embodiment, the bioluminescent protein is a mutated firefly Luciferase protein. Additional details regarding the mutated firefly Luciferase protein are described below and in the example.

Embodiments of the disclosure relate to using the split protein self complementing system to detect, study, monitor, evaluate, and/or screen biological events. In particular, embodiments of the present disclosure can be used to detect (and visualize) and quantitate biological events in in vitro as well as in in vivo studies, which can decrease time and expense since the same system can be used for cells and living organisms. Embodiments of the present disclosure can be used to test an event occurrence in a large number of samples, and has the capacity to transition from single cells to living animals without changing the imaging device.

In an embodiment, a first self complementing fragment is associated (e.g., biologically (e.g., bound to or expressed in), chemically, and/or physically) to a first target (e.g., a protein, a peptide, a cell (e.g., inside of or outside of), an organelle, tissue, a drug, a macromolecule, and the like), while a second self complementing fragment is associated with a second target or system. Then, if the first self complementing fragment and the second self complementing fragment come into contact with one another, they spontaneously self complement (e.g., inherent self affinity between the protein fragments brings the fragments close to each other and generates an event called complementation, as described in more detail below) to form a bioluminescent protein. The bioluminescent protein can produce a bioluminescent emission upon interaction with a bioluminescence initiating compound.

Split Protein Self Complementing Fragment Systems and Methods of Use

As mentioned above, embodiments of the disclosure relate to using split protein self complementing fragments of the firefly Luciferase to detect, study, monitor, evaluate, and/or screen biological events and/or interactions. In general, a first self complementing fragment (N-terminal fragment of the firefly Luciferase) is associated (e.g., biologically (e.g., bound to or expressed in), chemically (e.g., ionic bond, covalent bond, hydrogen bonding, and the like), and/or physically) to a first target or system (e.g., a protein, a peptide, a cell (e.g., inside of or outside of), an organelle, a drug, a macromolecule, and the like), while a second self complementing fragment (C-terminal fragment of the firefly Luciferase) is associated with a second target or system. The first and second self complementing fragments can be introduced into a system (e.g. inside a cell or outside a cell) and/or the first and/or the second self complementing fragments can be expressed (e.g., using a vector or other expression system) in the system.

Then, if the first self complementing fragment and the second self complementing fragment of firefly luciferase come into contact with one another as a result of the first target and second target interacting with one another, the fragments spontaneously self complement to form a bioluminescent firefly Luciferase protein (e.g., inherent self affinity between the N- and C-terminal fragments of a monomeric firefly luciferase protein brings the fragments close to each other and generates an event called complementation). The bioluminescent firefly Luciferase protein can produce a bioluminescent emission upon interaction with the bioluminescence initiating compound.

In an embodiment, the split protein self complementing fragments are used in methods of detecting protein-protein interaction. The first protein includes, but is not limited to, a first target protein and a first self complementing fragment. The first self complementing fragment includes a first portion of a firefly Luciferase protein, as described in more detail herein. The second protein includes, but is not limited to, a second target protein and a second self complementing fragment. The second self complementing fragment includes a second portion of a firefly Luciferase protein. The first target protein and the second target protein are proteins of interest in regard to protein-protein interaction in a system. A bioluminescent signal can be generated if the first target protein and the second target protein interact. In this regard, the first self complementing fragment and the second self complementing fragment spontaneously self complement in the presence of a bioluminescence initiating compound and produce the bioluminescent signal. Therefore, protein-protein interactions can be detected, studied, monitored, and/or evaluated.

In another embodiment, the split protein self complementing fragments are used in methods of the cellular localization of proteins. This system provides an easy and a quantitative readout when compared to other techniques in use for this purpose. Even though much study has been conducted to understand the functional aspects of cells, still many questions remain. In addition, many cellular networks function by movement of proteins from one compartment to another. Embodiments of the split protein self complementing fragments and systems can be used to identify nucleocytoplasmic and intra- and inter-compartment movement of proteins inside the cell.

In general, the method includes, but is not limited to, a first protein and a second protein. The first protein includes, but is not limited to, a first target protein and a first self complementing fragment. The first self complementing fragment includes a first portion of a firefly Luciferase protein, as described in more detail herein. The first protein is exposed to a cell. A compartment (e.g., organelle) of the cell includes (e.g., expressed in) a second protein including a second self complementing fragment. The second self complementing fragment includes a second portion of the firefly Luciferase protein that is complementary with the first self complementing fragment. The first self complementing fragment and the second self complementing fragment are not bioluminescent. When brought into contact with one another, the first self complementing fragment and the second self complementing fragment spontaneously self complement to substantially form the firefly Luciferase protein. A bioluminescent signal can be generated if the first protein containing the first target enters the compartment containing the second protein in the presence of a bioluminescence initiating compound. Therefore, the cellular localization of the target protein can be detected, studied, monitored, and/or evaluated.

In another embodiment, the split protein self complementing fragments are used in methods of monitoring cell fusion. Stem cell therapy has become a very useful strategy for treatment of many diseases. Still there is no clear evidence to support the mechanism by which stem cells differentiate into particular types of lineages. There are many views regarding this including 1). cell-cell fusion, and 2). selective induction by the cellular chemical released by the co-cultured cells. Even though cell-cell fusion has been studied by using selective markers, embodiments of the self complementing firefly luciferase fragments can provide more quantitative data for this event.

In general, the method includes, but is not limited to, a first cell and a second cell. The first cell includes (e.g., expressed in), but is not limited to, a first self complementing fragment. The first self complementing fragment includes a first portion of a firefly Luciferase protein. The second cell includes, but is not limited to, a second self complementing fragment. The second self complementing fragment includes a second portion of a firefly Luciferase protein that is complementary to the first self complementing fragment.

The first cell and the second cell are co-cultured together. If cell-cell fusion between the first cell and the second cell occurs, a bioluminescent signal is generated in the presence of a bioluminescence initiating compound.

Embodiments of this method may find application in stem cell research to determine the transformation from undifferentiated stem cells to adult differentiated specialized cells.

In another embodiment, the split protein self complementing fragments are used in methods of screening macromolecular delivery vehicles. The success of gene therapy depends on many different factors such as: developing efficient vectors that express defective genes for a long time, selective expression in a particular cell type, and developing an efficent cell delivery vehicle. This kind of selective cell delivery can be achieved, for example, by using cationic liposomes, basic peptides, and polyethylemine. To evaluate these molecules, embodiments of the split protein self complementing fragments and systems can be used as fusion proteins or as a mixture.

In general, the method includes, but is not limited to, a first protein and a cell that includes (e.g., expressed in) a second protein. The first protein includes, but is not limited to, a first target (e.g., a delivery vehicle) and a first self complementing fragment. The first self complementing fragment includes a first portion of a firefly Luciferase protein. The second protein includes, but is not limited to, a second self complementing fragment. The second self complementing fragment includes a second portion of the firefly Luciferase protein that is complementary to the first self complementing fragment. The first self complementing fragment and the second self complementing fragment are not bioluminescent. The first self complementing fragment and the second self complementing fragment spontaneously self complement upon introduction to one another to substantially form the firefly Luciferase protein.

The first protein is exposed to the cell including the second self complementing fragment. If the first target enters the cell in the presence of a bioluminescence initiating compound, a bioluminescent signal is generated. Therefore, if a bioluminescent signal is generated, the first target may be a candidate for a macromolecular delivery vehicle.

In another embodiment, the split protein self complementing fragments are used in methods of detecting phosphorylation. Protein phosphorylation controls the functional activity of many cellular proteins. So far, only the phosphospecific antibody has been used to identify this event, and this approach is restricted to cell lysates and intact cells. Embodiments of the self complementing firefly luciferase fragments in combination with a rigid linker can be used to construct vector expressing fusion proteins containing phosphorylation specific interacting proteins. This system can be studied in cell lysates, intact cells, and living animals.

In general, the method includes a structure such as, but not limited to, a first self complementing fragment, a phosphotyrosine binding substrate, a linker peptide, a phosphotyrosine peptide, and a second self complementing fragment. A phosphotyrosine binding substrate is attached to a first end of the first self complementing fragment. A phosphotyrosine peptide is attached to the first end of the second self complementing fragment.

In an embodiment, the linker peptide is attached to each of the phosphotyrosine binding substrate and the phosphotyrosine peptide to form a continuous structure in the following order: the first self complementing fragment, the phosphotyrosine binding substrate, the linker peptide, the phosphotyrosine peptide, and the second self complementing fragment. The linker peptide is rigid so as to separate the first self complementing fragment and the second self complementing fragment until phosphorylation is initiated between the phosphotyrosine binding substrate and the phosphotyrosine peptide. The first self complementing fragment and the second self complementing fragment are not bioluminescent. The first self complementing fragment and the second self complementing fragment can spontaneously self complement to substantially form the firefly Luciferase protein under appropriate conditions.

The structure is placed in conditions that may initiate phosphorylation between the phosphotyrosine binding substrate the phosphotyrosine peptide. A bioluminescent signal in the presence of a bioluminescence initiating compound is generated if phosphorylation occurs between the phosphotyrosine binding substrate the phosphotyrosine peptide. Therefore, the first self complementing fragment and the second self complementing fragment can be used as a sensor to detect phosphorlyation.

In embodiments of the present disclosure described above, a pair of compounds (e.g., a protein pair, a chemical compound pair, and the like) can be associated (e.g., biologically, chemically, physically) with each of the first protein and the second protein (or the first self complementing fragment and the second self complementing fragment) to assist the first and second protein into coming into contact with one another or within proximity of one another so that the first self complementing fragment and the second self complementing fragment can self complement with one another.

Split Protein Self Complementing Fragments

As mentioned above, the split protein self complementing fragments are not bioluminescent when separated. However, the split protein self complementing fragments are able to spontaneously self complement upon coming into close enough proximity to recover the substrate binding property or coming in contact with one another to form a bioluminescent firefly Luciferase protein. The bioluminescent firefly Luciferase protein can be bioluminescent upon interaction with a bioluminescence initiating compound.

Each of the split protein self complementing fragments are obtained from the firefly Luciferase protein (amino acids 1-550 of SEQ ID NO: 2) and conservatively modified variants thereof. The protein or split protein can be derived from polynucleotide sequence SEQ ID NO: 1 and degenerate variants thereof. The split protein self complementing fragments include portions, or conservatively modified variants thereof, of the firefly Luciferase protein. The protein and/or genetic sequences are described in the Example and figures. The split protein self complementing fragments may include, but are not limited to, a N fragment (e.g., 1 to 475 og SEQ ID NO: 2) or a C fragment (e.g., 245-300 to 550 of SEQ ID NO: 2) of the firefly Luciferase protein or conservatively modified variants of each. In particular, split protein self complementing fragments may include, but are not limited to, a Nfluc fragment (1-475 of SEQ ID NO: 2), a Nfluc fragment (1-455 of SEQ ID NO: 2), a Nfluc fragment (1-450 of SEQ ID NO: 2), a Cfluc fragment (245-550 of SEQ ID NO: 2), a Cfluc fragment (265-550 of SEQ ID NO: 2), a Cfluc fragment (300-550 of SEQ ID NO: 2), a Cfluc fragment (310-550 of SEQ ID NO: 2), and a Cfluc fragment (325-550 of SEQ ID NO: 2) or conservatively modified variants of each.

The firefly Luciferase protein or the split protein self complementing fragments can include conservatively modified variants as long as the conservatively modified variant retains the characteristics of the firefly Luciferase protein or the split protein self complementing fragments. It should be noted that polynucleotides encoding the conservatively modified variants are intended to be disclosed by this disclosure. Additional detail concerning the firefly Luciferase protein and self complementing fragments thereof are described in more detail in the Example below.

The split protein self complementing fragments can be included in a protein such as a fusion protein. For example, the fusion protein can include the split protein of one of the self complementing fragments, while also including a protein of interest and/or other proteins, linker, and/or other components consistent with the teachings of this disclosure. The split protein self complementing fragments or a protein including the split protein self complementing fragment can be expressed in a system (e.g., a cell) using a vector or other expression system or method, for example.

Note that for each protein, fusion protein, protein fragment, and nucleotide, one skilled in the art would be able to determine the corresponding nucleotide sequence or protein sequence, respectively. In addition, methods know in the art can be used to produce proteins, fusion proteins, protein fragments, nucleotides, vectors, and the like.

Self Complementing Fragment Vector

Each of the self complementing fragments or the fusion protein vectors can include, but are not limited to, polynucleotides (SEQ ID NO: 1) that encode the fragments of the firefly Luciferase as described above and degenerate nucleotide sequences thereof. Methods of producing vectors and other expression systems/methods are well known in the art.

Bioluminescence initiating compound

The bioluminescence initiating compound can include, but is not limited to, D-Luciferin, functional derivatives thereof, and other appropriate bioluminescence initiating compounds.

Additional Methods of Use

In another embodiment, the split protein self complementing fragments and methods described herein can be used to monitor and assess biological interactions by modifying vector constructs (e.g., protein-protein interaction, cell-cell fusion, screening macromolecular delivery vehicles, phosphorylation, and the like) in a transgenic animal.

In another embodiment, a cell line or transgenic animal is marked with vector sets described herein that are developed utilizing coding regions for the two proteins of interest, for example, followed by optical imaging to quantify protein-protein interaction in the presence and absence of pharmaceuticals designed to modulate the interaction. As will be appreciated by the skilled practitioner, this technique will significantly accelerate drug validation by allowing testing in vivo.

In this regard, the present disclosure also includes transgenic animals comprising exogenous DNA incorporated into the animal's cells to effect a permanent or transient genetic change, preferably a permanent genetic change. Permanent genetic change is generally achieved by introduction of the DNA into the genome of the cell. Vectors for stable integration include plasmids, retroviruses and other animal viruses, YACS, and the like. Generally, transgenic animals are mammals, most typically mice.

The exogenous nucleic acid sequence may be present as an extrachromosomal element or stably integrated in all or a portion of the animal's cells, especially in germ cells.

Unless otherwise indicated, a transgenic animal includes stable changes to the GERMLINE sequence. During the initial construction of the animal, chimeric animals (chimeras) are generated, in which only a subset of cells have the altered genome. Chimeras may then be bred to generate offspring heterozygous for the transgene. Male and female heterozygotes may then be bred to generate homozygous transgenic animals.

Typically, transgenic animals are generated using transgenes from a different species or transgenes with an altered nucleic acid sequence. For example, a human gene may be introduced as a transgene into the genome of a mouse or other animal. The introduced gene may be a wild-type gene, naturally occurring polymorphism, or a genetically manipulated sequence, for example having deletions, substitutions or insertions in the coding or non-coding regions.

For example, an introduced transgene may include genes corresponding to split protein self complementing fragments, such as a split firefly Luciferase gene, which may become functional via complementation or reconstitution when exposed to appropriate test proteins or, alternatively, which may become non-functional when exposed to a particular test protein that blocks complementation or reconstitution. Such a transgene, when introduced into a transgenic animal or cells in culture, is useful for testing potential therapeutic agents known or believed to interact with a particular target protein implicated in a disease or disorder. Where the introduced gene is a coding sequence, it is usually operably linked to a promoter, which may be constitutive or inducible, and other regulatory sequences required for expression in the host animal.

Transgenic animals can be produced by any suitable method known in the art, such as manipulation of embryos, embryonic stem cells, etc. Transgenic animals may be made through homologous recombination, where the endogenous locus is altered. Alternatively, a nucleic acid construct is randomly integrated into the genome. Vectors for stable integration include plasmids, retroviruses and other animal viruses, YACS, and the like.

Numerous methods for preparing transgenic animals are now known and others will likely be developed. See, e.g., U.S. Pat. Nos. 6,252,131, 6,455,757, 6,028,245, and 5,766,879, all incorporated herein by reference. Any method that produces a transgenic animal expressing a reporter gene following complementation or reconstitution is suitable for use in the practice of the present invention. The microinjection technique is particularly useful for incorporating transgenes into the genome without the accompanying removal of other genes.

Kits

This disclosure encompasses kits, which include, but are not limited to, split protein self complementing fragments; fusion proteins including a split protein self complementing fragment, split protein self complementing fragment vectors or fusion protein vectors; bioluminescence initiating compounds; and directions (written instructions for their use). The components listed above can be tailored to the particular biological event to be monitored as described herein. In addition, the components listed above can be tailored to the particular methods as described above. The kit can further include appropriate buffers and reagents known in the art for administering various combinations of the components listed above to the host cell or host organism.

EXAMPLE

Now having described the embodiments of the disclosure, in general, the example describes some additional embodiments. While embodiments of present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Introduction

Self-complementing reporter protein fragments may have applications in many areas of basic science research including but not limited to: 1) The identification of cellular localization of proteins where the study protein can be linked with one fragment of the reporter protein and the second fragment can be linked with different known cellular localization signals; 2) The study of macromolecular cellular delivery vehicles where one fragment will be stably expressed in the cells and the second fragment will be delivered by the delivery vehicle, which will avoid the problems associated with signals that don't allow precise knowledge of the location of the delivery vehicle; 3) The development of phosphorylation sensors where conformational changes induced by a phosphorylation event can lead to complementation.

In this study we identified suitable sites from the crystal structure of the firefly luciferase enzyme to generate rational fragments of monomeric reporter protein firefly luciferase that can produce self-complementation. We studied several different sites designed in different locations including: loops, α-helices and β-pleated sheets. We also proved that the co-localization in the same cellular compartment of both fragments of the enzyme is essential for complementation. We tested the efficiency of this system in different cell lines and the ability to image with sufficient sensitivity from cells implanted in living mice.

Experimental Procedures

Chemicals, Enzymes and Reagents: Restriction and modification enzymes and T4 DNA ligase were purchased from New England Biolabs (Beverly, Mass.). PCR amplification was performed with TripleMaster Taq DNA polymerase purchased from Brinkmann Eppendorf (Hamburg, Germany). PCR amplification was used for generating the rational fragments of N and C portions of firefly luciferase gene for each split points using the primers mentioned in Table 1 and the template plasmid pG5-Luc purchased from Promega (Madison, Wis.). Superfect transfection reagents, plasmid extraction kits, and DNA gel extraction kits were purchased from Qiagen (Valencia, Calif.). Coelenterazine was purchased from Biotium (Hayward, Calif.) and D-luciferin from Xenogen (Alameda, Calif.). Bacterial culture media were purchased from BD Diagnostic Systems (Sparks, Md.). All animal cell culture media, fetal bovine serum, antibiotics (streptomycin and penicillin) and plastic wares for growing cell cultures were purchased from Invitrogen (Carlsbad, Calif.). Rapamycin was purchased from Sigma (St. Louis, Mo.). The NCBI protein structure using the cn3D online software (Version 4.1, NCBI) was used to locate the split sites of firefly luciferase enzyme.

Construction of Plasmids: The N and C portions of firefly luciferase fragments for the selected 10 sites (generates 17 fragments: 7 Nfluc fragments & 10 Cfluc fragments), as shown in FIG. 1, were amplified using the primers listed in Table 1 and the template pG5-Luc plasmid of Promega's two-hybrid kit reporter. The forward primers of all N and C fragments were designed with Nhe I restriction enzyme site to allow for convenient cloning, and also with the Kozak sequence and start codon, for ribosome binding and initiation of translation respectively. The reverse primers were designed with stop codon and Xho I restriction enzyme site. The amplified fragments of each site were cloned in the corresponding restriction enzyme digested pcDNA3.1 (+) vector backbone (Invitrogen, CA-92008). The sequence confirmed clones from each site were used for further studies. The Nfluc (1-475 of SEQ ID NO: 2) and Cfluc (265-550 of SEQ ID NO: 2) fragments were also cloned with nuclear localization signal peptide (NLS of SV40 T antigen) at the N-terminal using the primer NLS-NF-Nfluc-475 and NLS-NF-Cfluc-265 (Table 1).

TABLE 1

The nucleotide sequence and the positions of PCR primers with linkers used for constructing different fragments of firefly luciferase enzyme generated for the study.

| Primer Name (SEQ ID. No) | Primer Sequence (5'→3') | Position |
|---|---|---|
| N-Forward Primer (3) | CTAGCTAGCATGGAAGACGCCAAAAACATAAAG | 1-24 |
| Nfluc Fragments | | |
| 415-Reverse Primer (4) | CCGCTCGAGTTAATCCTTGTCAATCAAGGCGTTGGT | 1245-1222 |
| 420-Reverse Primer (5) | CCGCTCGAGTTAAGAATGTAGCCATCCATCCTTGTC | 1260-1237 |
| 437-Reverse Primer (6) | CCGCTCGAGTTAGCGGTCAACGATGAAGAAGTGTTC | 1311-1288 |
| 445-Reverse Primer (7) | CCGCTCGAGTTATTTGTACTTAATCAGAGACTTCAG | 1335-1312 |
| 455-Reverse Primer (8) | CCGCTCGAGTTATTCCAATTCAGCGGGAGCCACCTG | 1365-1342 |

TABLE 1-continued

The nucleotide sequence and the positions of PCR primers with linkers used for constructing different fragments of firefly luciferase enzyme generated for the study.

| Primer Name (SEQ ID. No) | Primer Sequence (5'→3') | Position |
|---|---|---|
| 475-Reverse Primer (9) | CCGCTCGAGTTAATCGTCGGGAAGACCTGCGACACC | 1425-1402 |
| 500-Reverse Primer (10) | CCGCTCGAGTTAATCCACGATCTCTTTTTCCGTCAT | 1500-1477 |
| *Non-Overlapping Ofluc Fragments* | | |
| 415-Forward Primer (11) | CTAGCTAGCATGGGATGGCTGCATTCTGGAGACATA | 1246-1269 |
| 420-Forward Primer (12) | CTAGCTAGCATGGGAGACATAGCTTACTGGGACGAA | 1261-1284 |
| 437-Forward Primer (13) | CTAGCTAGCATGGTGAAGTCTCTGATTAAGTACAAAG | 1312-1336 |
| 445-Forward Primer (14) | CTAGCTAGCATGGGCTATCAGGTGGCTCCCGCTGAA | 1336-1359 |
| 455-Forward Primer (15) | CTAGCTAGCATGGCCATCTTGCTCCAACACCCCAACA | 1366-1390 |
| 475-Forward Primer (16) | CTAGCTAGCATGGACGCCGGTGAACTTCCCGCCGCC | 1426-1449 |
| 500-Forward Primer (17) | CTAGCTAGCATGGACGTCGCCAGTCAAGTAACAACCG | 1501-1525 |
| *Overlapping Ofluc Fragments* | | |
| 245-Forward Primer (18) | CTAGCTAGCATGGGTTTTGGAATGTTTACTACACTCG | 736-760 |
| 265-Forward Primer (19) | CTAGCTAGCATGGATAGATTTGAAGAAGAGCTGTTTC | 796-820 |
| 300-Forward Primer (20) | CTAGCTAGCATGGTTGACAAATACGATTTATCTAATT | 901-925 |
| C-Reverse Primer (21) | CCGCTCGAGTTACACGGCGATCTTTCCGCCCTTCTT | 1653-1627 |
| NLS-Nfluc-Forward (22) | CCGGCTAGCATG-NLS-GAAGACGCCAAAAACATAAAG | 1-24 |
| NLS-Cfluc-Forward (23) | CCGCTCGAGTTA-NLS-ATCCTTGTCAATCAAGGCGTT | 217-236 |

Note:
Bolded bases indicate either restriction enzyme site with start codon or stop codon.

Cell Culture: Human embryonic kidney cancer cells, 293T (ATCC, Manassas, Va.) were grown in MEM supplemented with 10% FBS and 1% penicillin/streptomycin solution. The $N_2a$ cells (Mouse neuroblastoma cells) were obtained from V. P. Mauro (Scripps Research Institute, La Jolla, Calif.) and CHO cells were grown in DMEM-Ham-F12-glutamax supplemented with 10% FBS and 1% penicillin/streptomycin. 3T3-L1 adipose cells were maintained in DMEM supplemented with 10% FBS and 1% penicillin/streptomycin/glutamine. HeLa cells were grown in MEM-high glucose supplemented with 10% FBS and 1% penicillin/streptomycin. SK-N-SH, SH-SY-5Y cells (ATCC, Manassas, Va.) were grown in MEM supplemented with 10% FBS/1 mM sodium pyruvate and 1% penicillin/streptomycin solution. MEM supplemented with 10% FBS/1 mM sodium pyruvate and 1% penicillin/streptomycin solution.

Cell Transfection and Luciferase Assay: Transfections were performed in 80% confluent 24 h old cultures of 293T, $N_2a$, HeLa, CHO, SK-N-SH, SH-SY5Y and 3T3-L1 cells. In 12 well plates, 250 ng/well of each plasmid was used for transfection. Volumes of Superfect used were as recommended by the manufacturer. The samples were assayed by mixing 20 µl of supernatant and 100 µl of substrate LARII from Promega by counting for 10 seconds in Turner 20/20 single tube luminometer. The readings were normalized by measuring the concentration of proteins from the cell lysates and represented as relative light units per microgram protein per minute. The transfection was normalized by co-transfecting 10 ng/well of pCMV-hRL DNA and measuring the *renilla* luciferase activity by using the substrate coelenterazine.

Imaging in Living Mice: To study bioluminescence imaging in living mice, the Nfluc fragment (1-475) found to give maximum signal with different Cfluc fragments [(245-550), (265-550), (300-550), (437-550), (445-550) and (500-550) of SEQ ID NO: 2] were used. Five million 293T cells transiently co-transfected with both N and C portions of the plasmid with different combinations were implanted subcutaneously in six different positions and imaged. The animals were repeatedly imaged at 0, 24, 48 and 72 h after implantation by using optical cooled coupled device camera (CCD) (Xenogen IVIS) to acquire the photons 10 minutes after intraperitoneal injection of 3 mg D-Luciferin dissolved in 100 µl of PBS. The bioluminescence signals were estimated by using the software Living Image (version 2.12) and are in units of photons per cubic centimeter per second per steradian ($P/cm^2/sec/sr$).

Results

Figure 3:
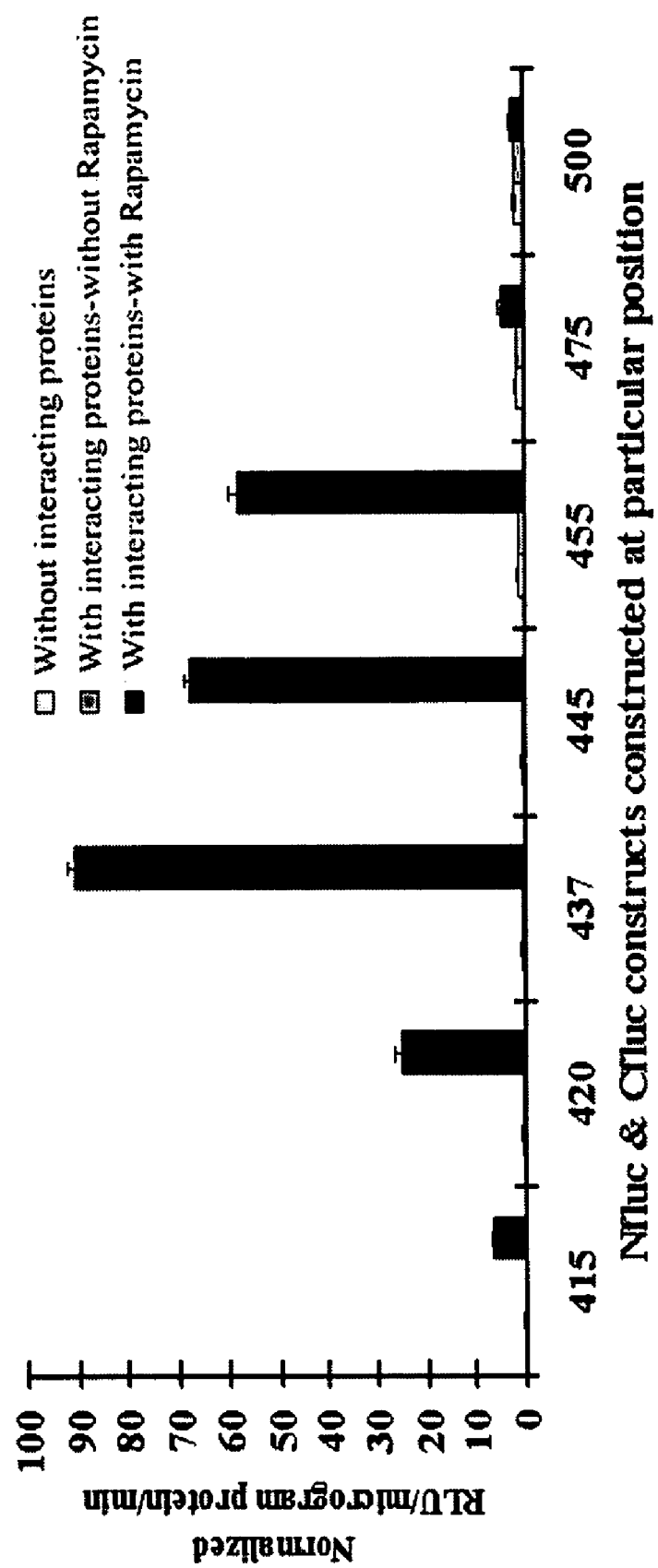
FIG. 3 illustrates luminometer results of different non-overlapping fragments with and without interacting proteins (FRB/FKBP12) studied in transiently transfected 293T cells and assayed 24 h post-transfection. The results are normalized by co-transfection of *renilla* luciferase. Four among the seven combinations showed significant signal upon exposure to rapamycin that brings Nfluc and Cfluc protein fragments together by interacting FRB and FKBP12 (split fragments generated at sites 420, 437, 445 and 445). The error bar is the standard error of the mean for three samples.

The non-overlapping fragments studied at seven different split sites showed significant protein-protein interaction mediated complementation from two of the seven sites:

To study the assisted (driven by two interacting proteins) and unassisted (self) complementation from different non-overlapping fragments of the firefly luciferase enzyme, seven different sites (amino acid positions 415, 420, 437, 445, 455, 475 and 500, each of SEQ ID NO: 2) were selected. Nfluc and Cfluc fragments (seven each), without any interacting proteins, and with rapamycin-mediated interacting proteins, FRB and FKBP12, were constructed and studied using the co-transfected 293T cells. The cells co-transfected with all seven combinations with FRB-Nfluc and Cfluc-FKBP12 show significant signal upon exposure to rapamycin only from the combinations of vectors constructed at split sites at amino acid positions 420, 437, 445 and 455, of SEQ ID NO: 2 (10±2 fold, 40±5 fold, 350±5 and 30±4 fold respectively over the cells not exposed to rapamycin). All seven combinations studied without interacting proteins and with interacting proteins but without rapamycin show signals that were not significantly different from mock-transfected cells (FIG. 3).

Figure 4:
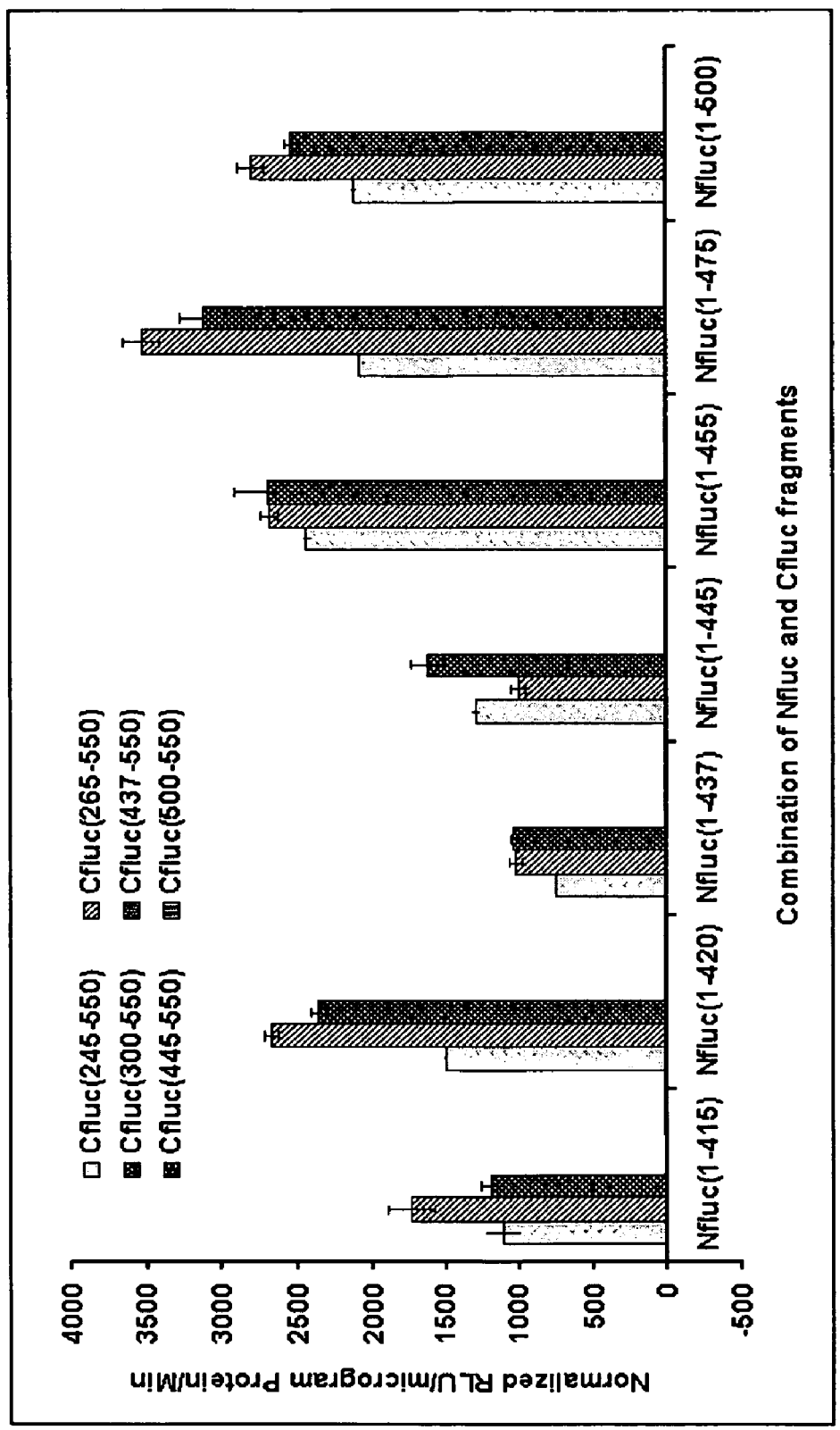
FIG. 4 illustrates luminometer assay conducted for different fragments generated for the fragment assisted self-complementation assay using 293T cells. The results are normalized for transfection efficiency using co-transfection of *renilla* luciferase. The result shows different levels of self-complementation associated luciferase activity resulting from different combinations of Nfluc and Cfluc fragments. The maximum level of activity was achieved from the cells co-transfected with Nfluc (amino acids 1-475 SEQ ID NO:2) and Cfluc (265-550 SEQ ID NO:2). The luciferase signals from cells co-transfected with the combination of Nfluc and Cfluc without overlapping sequences were not significantly different from mock-transfected cells. At the same time, many combinations of overlapping fragments showed enzyme activity that was significantly ($p<0.05$) above mock-transfected cells upon co-transfection. The error bar is the standard error of the mean for three samples.

Self-complementation of firefly luciferase enzyme fragments was achieved from different overlapping fragments and the highest signal was achieved from cells co-transfected with Nfluc (1-475 of SEQ ID NO: 2) and Cfluc (265-550 of SEQ ID NO: 2):

To identify the firefly luciferase protein fragments that give complementation-assisted recovery of luciferase enzyme activity, 13 different sites including 7 for generating Nfluc and Cfluc fragments, and 6 for generating only Cfluc fragments were identified by analyzing the crystal structure of the protein (FIG. 1). Co-transfection of each of the Nfluc fragments separately with all Cfluc fragments was studied using transiently transfected 293T cells. The result shows different levels of self-complementation based luciferase activity from different combinations of Nfluc and Cfluc fragments. The maximum level of activity was achieved from the cells co-transfected with the overlapping fragments Nfluc (1-475 of SEQ ID NO: 2) and Cfluc (265-550 of SEQ ID NO: 2). The levels of activity achieved from different combinations of fragments co-transfected cells ranged from 0.123 RLU/μg proteins/min [Nfluc (1-445 of SEQ ID NO: 2) and Cfluc (445-550 of SEQ ID NO: 2)] to as high as 3500 RLU/μg protein/min [Nfluc (1-475 of SEQ ID NO: 2) and Cfluc (265-550 of SEQ ID NO: 2)]. The cells co-transfected with the combination of Nfluc and Cfluc without overlapping sequences show signals that were not significantly different ($p<0.05$) from mock-transfected cells. At the same time, 65% of overlapping fragments showed enzyme activity that was significantly ($p<0.05$) above mock transfected cells upon co-transfection (FIG. 4). The results were normalized for transfection efficiency by co-transfecting pCMV-hRL and assaying for *renilla* luciferase activity.

The se/f-complementation of Nfluc (1-475 of SEQ ID NO: 2) with different Cfluc fragments at different time points showed different levels of enzyme activity by different combinations.

Figure 5:
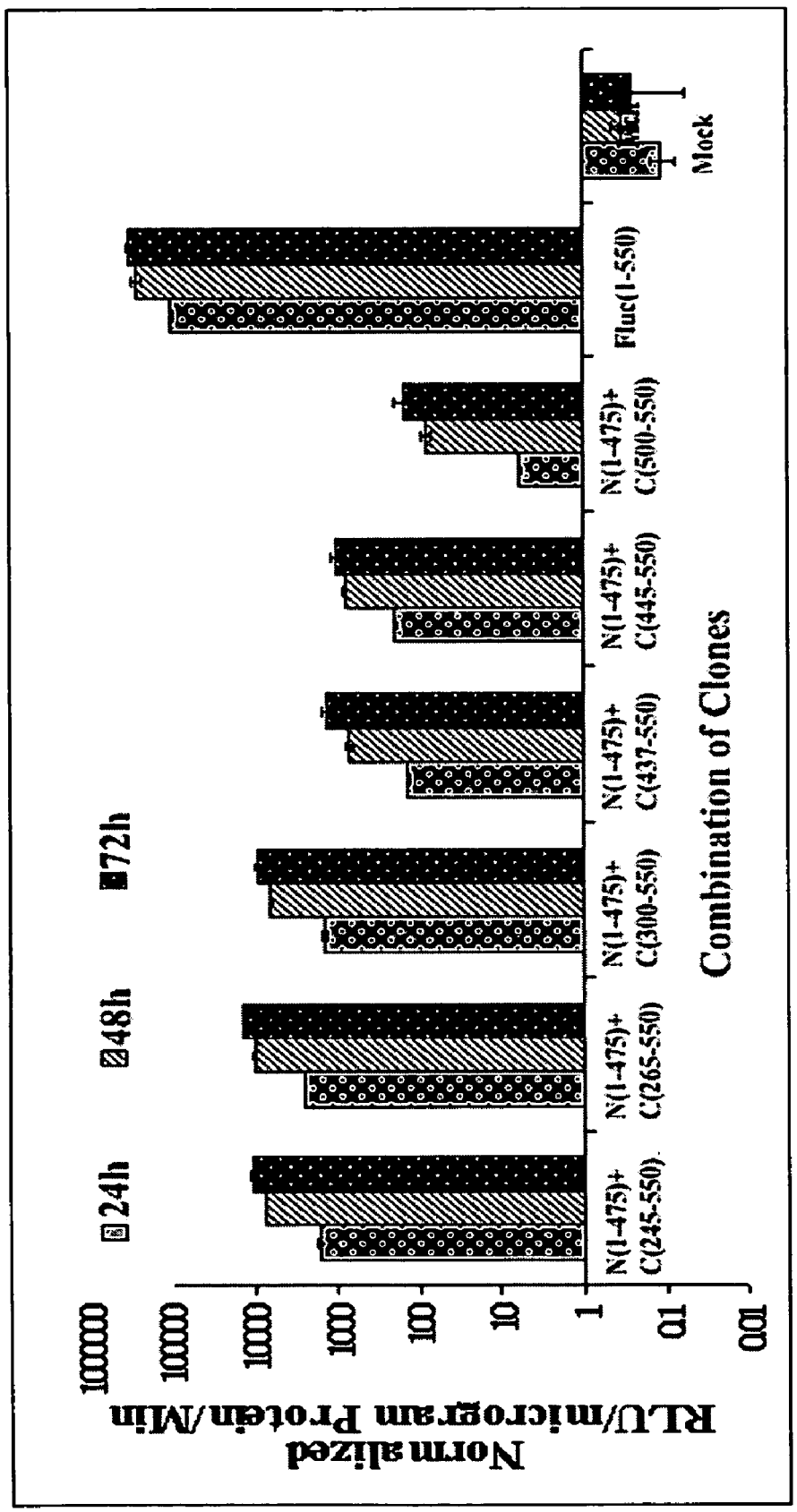
FIG. 5 illustrates a luminometer assay conducted for the 293T cells co-transfected with different combinations of Nfluc and Cfluc fragments studied at different time points (24 h, 48 h and 72 h). The results are normalized using co-transfection of *renilla* luciferase. The result shows significant ($p<0.05$) complementation assisted firefly luciferase enzyme activity from different Nfluc fragments with three Cfluc fragments (245-550, 265-550 and 300-550 of SEQ ID NO:2) at all three time points studied. There is a slight increase in the activity from 24 to 48 h (significant $p<0.05$) time point and no significant increase at 72 h. The error bar is the standard error of the mean for three samples.

To assess the efficiency of complementation as a function of time, 293T cells were co-transfected with Nfluc (1-475 of SEQ ID NO: 2) with different combination of Cfluc fragments (245-550, 265-550, 300-550, 437-550, 445-550 and 500-550, each of SEQ ID NO: 2) and assayed 24 h, 48 h and 72 h after co-transfection. The results show the greatest activity from cells co-transfected with Nfluc (1-475 of SEQ ID NO: 2) and Cfluc (265-550 of SEQ ID NO: 2) at each of the different time points studied. The signal observed by this combination was significantly higher ($p<0.05$) than all other combinations at all three-time points studied. There was a slight increase in the activity with increasing time (FIG. 5).

Self-complementation based recovery of luciferase enzyme activity was efficiently achieved in all the different cell lines studied.

Figure 6:
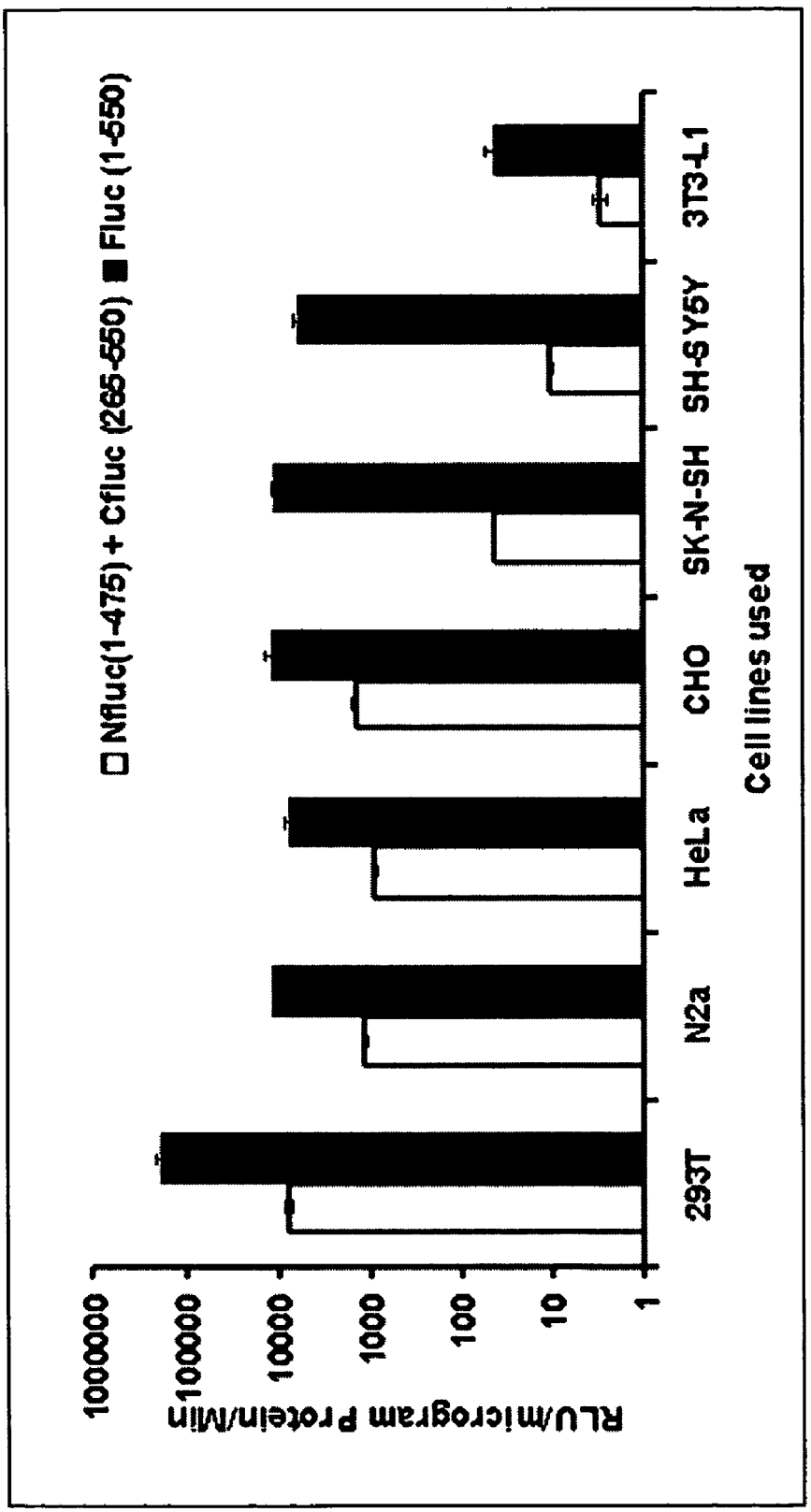
FIG. 6 illustrates a luminometer assay conducted for the combination of Nfluc (1-475 of SEQ ID NO:2) and Cfluc (265-550 of SEQ ID NO:2) as compared to fully intact fluc (1-550) in 293T, $N_2a$, HeLa, CHO, SK-N-SH, SH-SY5Y and 3T3-L1 cells. The result shows significant ($p<0.05$) fragments self-complementation assisted firefly luciferase enzyme activity in all cell lines as compared to mock-transfected cells. The error bar is the standard error of the mean for three samples.

To test the self-complementation assisted recovery of luciferase enzyme activity in different cell lines, the optimal combination of fragments Nfluc (1-475 of SEQ ID NO: 2) and Cfluc (265-550 of SEQ ID NO: 2) were studied in seven different cell lines; 293T, $N_2a$, HeLa, CHO, SK-N-SH, SH-SY5Y and 3T3-L1 cells. The cells were assayed for luciferase enzyme activity 24 h after transfection. The results show efficient self-complementation assisted luciferase enzyme activity in all the different cell lines studied. The result shows different levels of activity across different cell lines before normalizing for transfection efficiency, and is found to be similar when normalized. The greatest level of activity was achieved with 293T cells. The complemented signal level, in different cell lines, was compared with the cells transfected with intact Fluc and ranged from 3.2-5% after normalizing for transfection (FIG. 6).

The self-complementation firefly luciferase system showed sufficient signal for optical cooled coupled device camera imaging in living mice implanted subcutaneously with cells.

Figure 7:
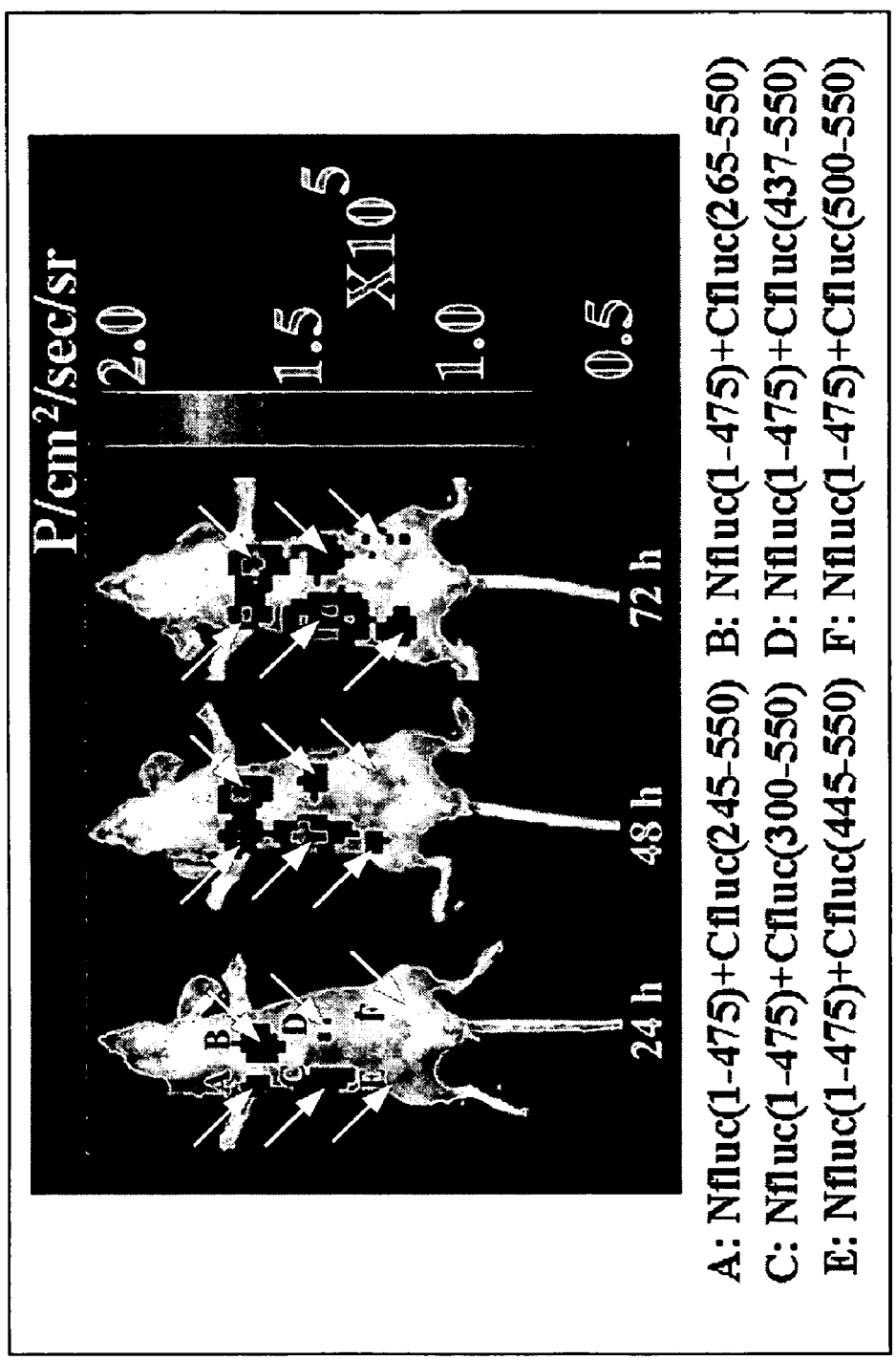
FIG. 7 illustrates in vivo imaging, using the optical CCD camera, that was conducted in mice with implants of 5 million cells co-transfected with Nfluc (1-475 of SEQ ID NO:2) and different Cfluc fragments in six different places: A (245-550 of SEQ ID NO:2), B (265-550 of SEQ ID NO:2), C (300-550 of SEQ ID NO:2), D (437-550 of SEQ ID NO:2), E (445-550 of SEQ ID NO:2) and F (500-550 of SEQ ID NO:2). The results show significant signal from the site implanted with the co-transfected Nfluc (1-475 of SEQ ID NO:2) with Cfluc (245-550 of SEQ ID NO:2), (265-550 of SEQ ID NO:2) and (300-550 of SEQ ID NO:2) in all time points studied. The other two combinations: Nfluc (1-475 of SEQ ID NO:2)/Cfluc (437-550 of SEQ ID NO:2) and Nfluc (1-475 of SEQ ID NO:2)/Cfluc (445-550 of SEQ ID NO:2) showed signals at the two higher time points studied. The cells co-transfected with the combinations of Nfluc (1-475 of SEQ ID NO:2) and Cfluc (500-550 of SEQ ID NO:2) showed no detectable signal at any of the time points studied.

To test the self-complementation assisted luciferase signal intensity in living animals, and also to determine the detectable limit of different combinations, we implanted 5 million 293T cells co-transfected with combination Fluc fragments: Nfluc (1-475 of SEQ ID NO:2) and different Cfluc fragments (245-550, 265-550, 300-550, 437-550, 445-550 and 500-550, each of SEQ ID NO: 2) subcutaneously in 6 different sites immediately after transfection. The animals (N=6) were imaged immediately (0 h), 24 h, 48 h and 72 h after implanting the cells by using optical CCD camera by injecting 3 mg of D-Luciferin i.p. The signals were quantified and compared with cell culture data. No signals were detected from any of the sites imaged immediately after implanting the cells. After 24 h, the sites implanted with cells co-transfected with Nfluc (1-475) and Cfluc [(245-550), (265-550) and (300-550), each of SEQ ID NO: 2] showed significant ($p<0.01$) signals (0.3±0.15 P/cm²/sec/sr) compared to the animals imaged immediately after implanting cells. At the 48 h time point, the site implanted with the cells co-transfected with Nfluc (1-475 of SEQ ID NO: 2) and Cfluc (437-550 of SEQ ID NO: 2) also showed signal that was significantly ($p<0.05$) above the background but not as high as the other three sites. All the sites other than the site where cells implanted with the cells co-transfected with non-overlapping Nfluc (1-475 of SEQ ID NO: 2) and Cfluc (500-550 of SEQ ID NO: 2) fragments showed significant detectable signal after 72 h, and the average of photon max estimated across six animals by the fragment combinations Nfluc (1-475)/Cfluc (245-550), Nfluc (1-475)/Cfluc (265-550), Nfluc (1-475)/Cfluc (300-550), Nfluc (1-475)/Cfluc (437-550), Nfluc (1-475)/Cfluc (445-550), Nfluc (1-475)/Cfluc (500-550) (of SEQ ID NO: 2) respectively are 1.1±0.4, 1.8±0.5, 1.9±0.3, 2.1±0.6, 0.7±0.42, 0.3±0.2 P/cm²/sec/sr (FIG. 7).

Figure 8:
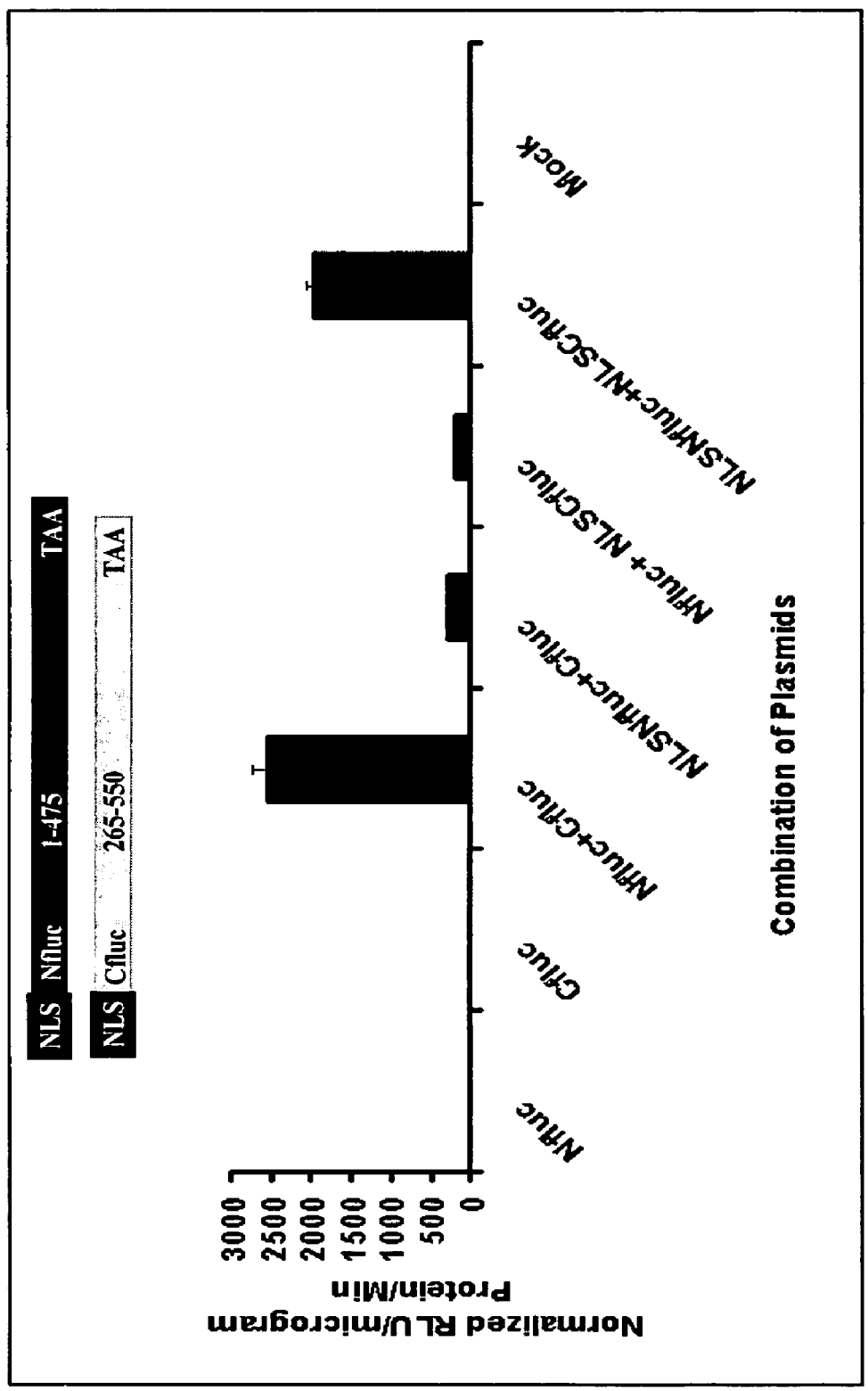
FIG. 8 illustrates a luminometer assay conducted for the firefly luciferase enzyme fragments complementation by compartmentalizing the fragments in the same cellular localization. The cells co-transfected with either both the fragments without NLS or with NLS showed significant signal (N+C). The cells co-transfected with the combinations fragments containing one fragment with NLS and the other without NLS showed signal that was significantly less (p<0.01) than the previous one (N+NLS−C and NLS−N+C). The error bar is the standard error of the mean for three samples.

The Firefly luciferase fragments self-complementation can be efficiently achieved by localizing both fragments in the same cellular compartment To use the firefly luciferase fragments self-complementation efficiently for the identification of interacting protein partners with unknown cellular localization and also for the identification of nuclear, mitochondrial and membrane transport of particular interacting protein pairs, we studied the interaction of the fragments expressing nuclear localizations signals. Nfluc (1-475 of SEQ ID NO: 2) and Cfluc (265-550 of SEQ ID NO: 2) fragments were expressed with NLS signal peptide of SV40 T antigen (PKKKRKVD) at amino terminal, and firefly luciferase activity was determined by co-transfecting 293T cells in different combinations as described above. The cells co-transfected with either both fragments without NLS or with NLS showed significant signals relative to mock transfection and cells transfected with individual fragments (with or without NLS). The cells co-transfected with the combination fragments containing one fragment with NLS and the other without NLS showed signal that was significantly less ($p<0.01$) than cells transfected with Nfluc+Cfluc or NLS–Nfluc+NLS–Cfluc (FIG. 8).

Discussion

A significant ($p<0.05$) amount of luciferase activity through fragment self-complementation was achieved only from 18 combinations of overlapping fragments that include different Nfluc fragments (1-415, 1-420, 1-437, 1-445, 1-475 and 1-500 of SEQ ID NO: 2) and Cfluc fragments (245-550, 265-550 and 300-550 of SEQ ID NO: 2). The fragments with greater overlap generally showed a higher signal, although this result did not hold true for some combinations of fragments examined. For example, in both cell culture and animal study, the luciferase signal from the combination of fragments selected with the greatest degree of overlap (Nfluc 1-475 encoded by the polynucleotide SEQ ID NO: 2)/(Cfluc 245-550 of SEQ ID NO: 2) was 2-fold less than that of the combination with less overlap [(Nfluc 1-475 of SEQ ID NO: 2)/(Cfluc 265-550 of SEQ ID NO: 2)]. Therefore, there does not appear to be any correlation between the degree of overlap and signal generated from complementation-assisted luciferase signal.

This system can be used to image protein-protein interactions along with different areas of basic cell biology research. The self-complementing fragments of the Cre recombinase enzyme have been efficiently used for temporally controlled recombination processes in cells. Although, the basic principles of splitting monomeric proteins for self-complementation and protein-protein interaction assisted complementation are the same, the utility of these protein fragments is entirely different. In the current study, for the first time, we generated a dimeric active firefly luciferase enzyme by generating many $NH_2$ and COOH terminal fragments. The firefly luciferase enzyme is a reporter molecule with many sensitive detection systems available for the quantification of protein activity both in cells and in living animals, the developed fragments self-complementation system will be useful in many different applications. A number of studies have been conducted for investigating the structural folding and the non-covalent interaction of complementing fragments of a protein using enzymes RNase A, cytochrome c, staphylococcal nuclease and β-galactosidase for different applications like, to see the evolutionary origin, temporal control of enzyme activity and for studying protein-protein interactions.

Advances in bioluminescence imaging using cooled charged coupled device (CCD) cameras are providing a highly sensitive means for imaging and quantifying very low levels of visible light from intact small living subjects. The design of a protein-fragment-assisted complementation assay entails the interaction of two proteins chimeras: each composed of one protein partner fused in frame with a split segment of a reporter protein. The interaction is driven by, and brings together the two protein partners, leading to the recovery of reporter activity through protein complementation of the two trailing split reporter segments. The developed system in the current study doesn't require protein-protein interaction in order to complement the reporter fragments, but in that case they should generally be in the same cellular compartment to achieve complementation. The self-complementing fragments developed in this study produce signal intensities that were enough to efficiently assay and image in cells and mice quantitatively. Intercellular, intracellular and nucleo-cytoplasmic trafficking of functional proteins plays a major role in regulating many cellular functions. Even though the functions of different proteins are determined by post-translational modification, the only way by which proteins trafficking within and between cells can be currently studied is by immunocytochemistry or by tagging with fluorescent proteins. However, the subcellular localization of proteins by these microscopic techniques is not suitable for quantitative analysis or for the high throughput screening of a larger number of samples. Hence, the strategy developed in this study compensates for both of these drawbacks and also provides an additional advantage for the use of this system in living animals via non-invasive imaging. This strategy may also have more applications along with the identification of proteins' cellular localization including studying macromolecular delivery systems, and for developing intracellular phosphorylation sensors.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and protected by the following claims.

```
SEQ ID NO: 1
Nucleotide sequence of full length firefly
luciferase (corresponding to amino acids 1-550)
atggaagacgccaaaaacataaagaaaggcccggcgccattctatccgct ggaagatggaaccgctggagagcaactgcataaggctatgaagagatacg ccctggttcctggaacaattgcttttacagatgcacatatcgaggtggac atcacttacgctgagtacttcgaaatgtccgttcggttggcagaagctat gaaacgatatgggctgaatacaaatcacagaatcgtcgtatgcagtgaaa actctcttcaattctttatgccggtgttgggcgcgttatttatcggagtt gcagttgcgcccgcgaacgacatttataatgaacgtgaattgctcaacag tatgggcatttcgcagcctaccgtggtgttcgtttccaaaaaggggttgc aaaaaattttgaacgtgcaaaaaaagctcccaatcatccaaaaaattatt atcatggattctaaaacggattaccagggatttcagtcgatgtacacgtt cgtcacatctcatctacctcccggttttaatgaatacgattttgtgccag agtccttcgatagggacaagacaattgcactgatcatgaactcctctgga tctactggtctgcctaaaggtgtcgctctgcctcatagaactgcctgcgt gagattctcgcatgccagagatcctattttggcaatcaaatcattccgg atactgcgattttaagtgttgttccattccatcacggttttggaatgttt actacactcggatatttgatatgtggatttcgagtcgtcttaatgtatag atttgaagaagagctgtttctgaggagccttcaggattacaagattcaaa gtgcgctgctggtgccaacccctattctccttcttcgccaaaagcactctg attgacaaatacgatttatctaatttacacgaaattgcttctggtggcgc tcccctctctaaggaagtcggggaagcggttgccaagaggttccatctgc caggtatcaggcaaggatatgggctcactgagactacatcagctattctg
```

-continued

```
attacacccgagggggatgatcaaaccgggcgcggtcggtaaagttgttcc atttttttgaagcgaaggttgtggatctggataccgggaaaacgctgggcg ttaatcaaagaggcgaactgtgtgtgagaggtcctatgattatgtccggt tatgtaaacaatccggaagcgaccaacgccttgattgacaaggatggatg gctacattctggagacatagcttactgggacgaagacgaacacttcttca tcgttgaccgcctgaagtctctgattaagtacaaaaggctatcaggtggct cccgctgaattggaatccatcttgctccaacaccccaacatcttcgacgc aggtgtcgcaggtcttcccgacgatgacgccggtgaacttcccgccgccg ttgttgttttggagcacggaaagacgatgacggaaaaagagatcgtggat tacgtcgccagtcaagtaacaaccgcgaaaaagttgcgcggaggagttgt gtttgtggacgaagtaccgaaaggtcttaccggaaaactcgacgcaagaa aaatcagagagatcctcataaaggccaagaagggcggaaagatcgccgtg taa
```

SEQ ID NO: 2

Polypeptide Sequence of Firefly Luciferase (Firefly Luciferase, *Photinus pyralis* (North American)):

```
  1 medaknikkg papfypledg tageqlhkam kryalvpgti aft-
    dahievn ityaeyfems
 61 vrlaeamkry glntnhrivv csenslqffm pvlgalfigv ava-
    pandiyn erellnsmni
121 sqptvvfvsk kglqkilnvq kklpiiqkii imdsktdyqg fqsmyt-
    fvts hlppgfneyd
181 fvpesfdrdk tialimnssg stglpkgval phrtacvrfs hardpif-
    gnq iipdtailsv
241 vpfhhgfgmf ttigylicgf rvvlmyrfee elfirsiqdy kiqsallvpt
    lfsffakstl
301 idkydlsnih eiasggapls kevgeavakr fhlpgirqgy gltettsail
    itpegddkpg
361 gvgkwpffe akwdidtgk tlgvnqrgel cvrgpmimsg yvn-
    npeatna lidkdgwlhs
421 gdiaywdede hffivdrlks likykgyqva paelesillq
    hpnifdagva glpdddagel
481 paavvvlehg ktmtekeivd yvasqvttak klrggvvfvd evp-
    kgltgkl darkireili
541 kakkggkskl
```

---

We claim the following:

1. A split protein system, comprising:
   a first protein including a first self complementing fragment, wherein the first self complementing fragment comprises an N-terminal fragment of a firefly Luciferase protein (Nfluc); and
   a second protein including a second self complementing fragment complementary with the first self complementing fragment, wherein the second self complementing fragment comprises a C-terminal fragment of a firefly Luciferase protein (Cfluc),
   wherein the Nfluc fragment and the Cfluc fragment include an overlap of 30 or more amino acids, and wherein the first self complementing fragment and the second self complementing fragment are not bioluminescent individually, and wherein the first self complementing fragment and the second self complementing fragment spontaneously self complement to substantially form the firefly Luciferase protein that is bioluminescent.

2. The split protein system of claim 1, wherein the first protein includes a first target protein and the first self complementing fragment.

3. The split protein system of claim 1, wherein the first protein includes a first target protein and the first self complementing fragment, and wherein the second protein includes a second target protein and the second self complementing fragment.

4. The split protein system of claim 1, wherein the Nfluc fragment includes at least amino acids 1-437 of SEQ ID NO: 2.

5. The split protein system of claim 1, wherein the Nfluc fragment includes amino acids 1-475 of SEQ ID NO: 2 and conservative variants thereof.

6. The split protein system of claim 1, wherein the Nfluc fragment includes amino acids 1-475 of SEQ ID NO: 2.

7. The split protein system of claim 1, wherein the Nfluc fragment includes amino acids 1-450 of SEQ ID NO: 2 and conservative variants thereof.

8. The split protein system of claim 1, wherein the Nfluc fragment includes amino acids 1-455 of SEQ ID NO: 2 and conservative variants thereof.

9. The split protein system of claim 1, wherein the firefly Luciferase protein (Cfluc) is selected from one of the following: a Cfluc fragment having amino acids 245-550 of SEQ ID NO: 2 and conservative variants thereof, Cfluc fragment having amino acids 265-550 of SEQ ID NO: 2 and conservative variants thereof, a Cfluc fragment having amino acids 300-550 of SEQ ID NO: 2 and conservative variants thereof, a Cfluc fragment having amino acids 310-550 of SEQ ID NO: 2 and conservative variants thereof, and a Cfluc fragment having amino acids 325-550 of SEQ ID NO: 2 and conservative variants thereof.

10. The split protein system of claim 1, wherein the N-terminal fragment is selected from: a Nfluc fragment having amino acids 1-475 of SEQ ID NO: 2 and conservative variants thereof, a Nfluc fragment having amino acids 1-455 of SEQ ID NO: 2 and conservative variants thereof, and a Nfluc fragment having amino acids 1-450 of SEQ ID NO: 2 and conservative variants thereof; and wherein the C-terminal fragment is selected from: a Cfluc fragment having amino acids 245-550 of SEQ ID NO: 1 and conservative variants thereof, a Cfluc fragment having amino acids 265-550 of SEQ ID NO: 2 and conservative variants thereof, a Cfluc fragment having amino acids 300-550 of SEQ ID NO: 2 and conservative variants thereof, a Cfluc fragment having amino acids 310-550 of SEQ ID NO: 2 and conservative variants thereof, and a Cfluc fragment having amino acids 325-550 of SEQ ID NO: 2 and conservative variants thereof.

11. The split protein system of claim 1, wherein the N-terminal fragment includes a Nfluc fragment having amino acids 1-475 of SEQ ID NO: 2 and conservative variants thereof, and the C-terminal fragment is selected from one of the following: a Cfluc fragment having amino acids 245-550 of SEQ ID NO: 2 and conservative variants thereof, Cfluc fragment having amino acids 265-550 of SEQ ID NO: 2 and conservative variants thereof, and Cfluc fragment having amino acids 300-550 of SEQ ID NO: 2 and conservative variants thereof.

12. A split protein system, comprising:
a first protein including a first self complementing fragment, wherein the first self complementing fragment comprises an N-terminal fragment of a firefly Luciferase protein (Nfluc) selected from one of the following: a Nfluc fragment having amino acids 1-475 of SEQ ID NO: 2 and conservative variants thereof, a Nfluc fragment having amino acids 1-455 of SEQ ID NO: 2 and conservative variants thereof, and a Nfluc fragment having amino acids 1-450 of SEQ ID NO: 2 and conservative variants thereof, and
a second protein including a second self complementing fragment complementary with the first self complementing fragment, wherein the second self complementing fragment comprises a C-terminal fragment of a firefly Luciferase protein (Cfluc) selected from one of the following: a Cfluc fragment having amino acids 245-550 of SEQ ID NO: 2 and conservative variants thereof, Cfluc fragment having amino acids 265-550 of SEQ ID NO: 2 and conservative variants thereof, a Cfluc fragment having amino acids 300-550 of SEQ ID NO: 2 and conservative variants thereof, a Cfluc fragment having amino acids 310-550 of SEQ ID NO: 2 and conservative variants thereof, and a Cfluc fragment having amino acids 325-550 of SEQ ID NO: 2 and conservative variants thereof.

13. The split protein system of claim 12, wherein the first protein includes a first target protein and the first self complementing fragment, and wherein the second protein includes a second target protein and the second self complementing fragment.

14. The split protein system of claim 12, wherein the Nfluc fragment includes amino acids 1-475 of SEQ ID NO: 2.

15. The split protein system of claim 12, wherein the Nfluc fragment includes amino acids 1-475 of SEQ ID NO: 2 and conservative variants thereof.

16. The split protein system of claim 12, wherein the Nfluc fragment includes amino acids 1-450 of SEQ ID NO: 2 and conservative variants thereof.

17. The split protein system of claim 12, wherein the Nfluc fragment includes amino acids 1-455 of SEQ ID NO: 2 and conservative variants thereof.

18. A split protein system, comprising:
a first protein including a first self complementing fragment, wherein the first self complementing fragment comprises an N-terminal fragment of a firefly Luciferase protein (Nfluc) having amino acids 1-475 of SEQ ID NO: 2 and conservative variants thereof, and
a second protein including a second self complementing fragment complementary with the first self complementing fragment, wherein the second self complementing fragment comprises a C-terminal fragment of a firefly Luciferase protein (Cfluc) selected from one of the following: a Cfluc fragment having amino acids 245-550 of SEQ ID NO: 2 and conservative variants thereof, Cfluc fragment having amino acids 265-550 of SEQ ID NO: 2 and conservative variants thereof, and Cfluc fragment having amino acids 300-550 of SEQ ID NO: 2 and conservative variants thereof.

19. The split protein system of claim 18, wherein the first protein includes a first target protein and the first self complementing fragment, and wherein the second protein includes a second target protein and the second self complementing fragment.

20. A split protein system, comprising:
a first protein including a first self complementing fragment, wherein the first self complementing fragment comprises an N-terminal fragment of a firefly Luciferase protein (Nfluc); and
a second protein including a second self complementing fragment complementary with the first self complementing fragment, wherein the second self complementing fragment comprises a C-terminal fragment of a firefly Luciferase protein (Cfluc),
wherein the Nfluc fragment and the Cfluc fragment include an overlap of 38 or more amino acids, and wherein the first self complementing fragment and the second self complementing fragment are not bioluminescent individually, and wherein the first self complementing fragment and the second self complementing fragment spontaneously self complement to substantially form the firefly Luciferase protein that is bioluminescent.

21. The split protein system of claim 20, wherein the N-terminal fragment of a firefly Luciferase protein (Nfluc) is an Nfluc fragment having amino acids 1-475 of SEQ ID NO: 2.

22. The split protein system of claim 20, wherein the N-terminal fragment of a firefly Luciferase protein (Nfluc) is an Nfluc fragment having amino acids 1-455 of SEQ ID NO: 2.

23. The split protein system of claim 20, wherein the N-terminal fragment of a firefly Luciferase protein (Nfluc) is an Nfluc fragment having amino acids 1-450 of SEQ ID NO: 2.

24. The split protein system of claim 20, wherein the N-terminal fragment of a firefly Luciferase protein (Nfluc) is an Nfluc fragment having amino acids 1-437 of SEQ ID NO: 2.

25. The split protein system of claim 20, wherein the N-terminal fragment of a firefly Luciferase protein (Nfl uc) is selected from one of the following: a Nfluc fragment having amino acids 1-475 of SEQ ID NO: 2 and conservative variants thereof, a Nfluc fragment having amino acids 1-455 of SEQ ID NO: 2 and conservative variants thereof, and a Nfluc fragment having amino acids 1-450 of SEQ ID NO: 2 and conservative variants thereof.

26. The split protein system of claim 20, wherein the firefly Luciferase protein (Cfluc) is selected from one of the following: a Cfluc fragment having amino acids 245-550 of SEQ ID NO: 2 and conservative variants thereof, Cfluc fragment having amino acids 265-550 of SEQ ID NO: 2 and conservative variants thereof, a Cfluc fragment having amino acids 300-550 of SEQ ID NO: 2 and conservative variants thereof, a Cfluc fragment having amino acids 310-550 of SEQ ID NO: 2 and conservative variants thereof, and a Cfluc fragment having amino acids 325-550 of SEQ ID NO: 2 and conservative variants thereof.

27. A split protein system, comprising:
- a first protein including a first self complementing fragment, wherein the first self complementing fragment comprises an N-terminal fragment of a firefly Luciferase protein (Nfluc); and
- a second protein including a second self complementing fragment complementary with the first self complementing fragment, wherein the second self complementing fragment comprises a C-terminal fragment of a firefly Luciferase protein (Cfluc),
- wherein the Nfluc fragment and the Cfluc fragment include an overlap of 175 or more amino acids, and wherein the first self complementing fragment and the second self complementing fragment are not bioluminescent individually, and wherein the first self complementing fragment and the second self complementing fragment spontaneously self complement to substantially form the firefly Luciferase protein that is bioluminescent.

28. The split protein system of claim 27, wherein the N-terminal fragment of a firefly Luciferase protein (Nfluc) is an Nfluc fragment having amino acids 1-475 of SEQ ID NO: 2.

29. The split protein system of claim 27, wherein the N-terminal fragment of a firefly Luciferase protein (Nfluc) is an Nfluc fragment having amino acids 1-455 of SEQ ID NO: 2.

30. The split protein system of claim 27, wherein the N-terminal fragment of a firefly Luciferase protein (Nfluc) is an Nfluc fragment having amino acids 1-450 of SEQ ID NO: 2.

31. The split protein system of claim 27, wherein the N-terminal fragment of a firefly Luciferase protein (Nfluc) is an Nfluc fragment having amino acids 1-437 of SEQ ID NO: 2.

32. The split protein system of claim 27, wherein the N-terminal fragment of a firefly Luciferase protein (Nfl uc) is selected from one of the following: a Nfluc fragment having amino acids 1-475 of SEQ ID NO: 2 and conservative variants thereof, a Nfluc fragment having amino acids 1-455 of SEQ ID NO: 2 and conservative variants thereof, and a Nfluc fragment having amino acids 1-450 of SEQ ID NO: 2 and conservative variants thereof.

33. The split protein system of claim 27, wherein the firefly Luciferase protein (Cfluc) is selected from one of the following: a Cfluc fragment having amino acids 245-550 of SEQ ID NO: 2 and conservative variants thereof, Cfluc fragment having amino acids 265-550 of SEQ ID NO: 2 and conservative variants thereof, a Cfluc fragment having amino acids 300-550 of SEQ ID NO: 2 and conservative variants thereof, a Cfluc fragment having amino acids 310-550 of SEQ ID NO: 2 and conservative variants thereof, and a Cfluc fragment having amino acids 325-550 of SEQ ID NO: 2 and conservative variants thereof.

* * * * *